(12) United States Patent
Whitaker et al.

(10) Patent No.: US 9,046,205 B2
(45) Date of Patent: Jun. 2, 2015

(54) FLUID CONNECTOR LATCHES WITH PROFILE LEAD-INS

(75) Inventors: Carl T. Whitaker, Berthoud, CO (US); Peter D. Lewis, Fort Collins, CO (US)

(73) Assignee: NORDSON CORPORATION, Westlake, OH (US)

( * ) Notice: Subject to any disclaimer, the term of this patent is extended or adjusted under 35 U.S.C. 154(b) by 306 days.

(21) Appl. No.: 12/976,894

(22) Filed: Dec. 22, 2010

(65) Prior Publication Data

US 2011/0204621 A1 Aug. 25, 2011

Related U.S. Application Data

(60) Provisional application No. 61/289,990, filed on Dec. 23, 2009, provisional application No. 61/361,306, filed on Jul. 2, 2010.

(51) Int. Cl.
*F16L 37/56* (2006.01)
*F16L 37/084* (2006.01)
*A61M 39/10* (2006.01)

(52) U.S. Cl.
CPC ............ *F16L 37/0841* (2013.01); *A61M 39/10* (2013.01); *A61M 39/1011* (2013.01); *A61M 39/105* (2013.01); *A61M 2039/1088* (2013.01); *F16L 37/56* (2013.01)

(58) Field of Classification Search
CPC .............................. F16L 37/0841; F16L 37/56
USPC ........... 285/124.1, 124.4, 314, 316, 317, 308; 904/905, 206, 326, 533; 604/905, 206, 604/326, 533
See application file for complete search history.

(56) References Cited

U.S. PATENT DOCUMENTS 163,261 A 5/1875 Ruppenthal
185,896 A 1/1877 Curtis
(Continued)

FOREIGN PATENT DOCUMENTS

BE 479098 1/1948
CN 101311603 11/2005
(Continued)

OTHER PUBLICATIONS

About Us [online], Thuro Metal Products [retrieved on Apr. 9, 2010], retrieved from the Internet: <URL: http://www.thurometal.com/about.html>, 2 pages.
(Continued)

*Primary Examiner* — David E Bochna
*Assistant Examiner* — James Linford
(74) *Attorney, Agent, or Firm* — Dorsey & Whitney LLP

(57) ABSTRACT

A female receiving connector for connecting sections of tubing is provided. The female receiving connector includes a housing having a top housing portion and a bottom housing portion coupled to the top housing portion. The female receiving connector also includes a button moveably coupled within the housing. A locking plate is coupled to the button and configured to move with the button. The locking plate has a profile lead-in having an interfacing surface located at a proximal side of the profile lead-in for interfacing a male connector. The interfacing surface extends along at least a portion of at least three sides of an aperture of the locking plate and is tapered along one or more of the at least three sides. Additionally, the profile lead-in includes a locking surface located at a distal side of the profile lead-in for securing the male connector within the housing of the female receiving connector. A substantially flat surface is located between the interfacing surface and the locking surface.

11 Claims, 12 Drawing Sheets

(56) References Cited

U.S. PATENT DOCUMENTS

| | | |
|---|---|---|
| 187,982 A | 3/1877 | Pirsson et al. |
| 200,944 A | 3/1878 | Smith |
| 235,580 A | 12/1880 | Smith et al. |
| 327,509 A | 10/1885 | Aldridge |
| 584,008 A | 6/1887 | Munson |
| 465,868 A | 12/1891 | List |
| 725,421 A | 4/1903 | Dinkins |
| 727,982 A | 5/1903 | Ludwig |
| 874,957 A | 12/1907 | Godley |
| 884,461 A | 4/1908 | Browne |
| 909,131 A | 1/1909 | Antic |
| 951,889 A | 3/1910 | Teuer |
| D42,368 S | 3/1912 | Mossberg |
| 1,029,819 A | 6/1912 | Nylander |
| 1,033,187 A | 7/1912 | Metzger |
| 1,039,354 A | 9/1912 | Bonadio |
| 1,077,417 A | 11/1913 | McCracken |
| 1,078,112 A | 11/1913 | Storm |
| 1,115,945 A | 11/1914 | Kunz |
| 1,193,446 A | 8/1916 | Wells |
| 1,239,345 A | 9/1917 | Brown |
| 1,255,847 A | 2/1918 | Arkin |
| 1,259,684 A | 3/1918 | Vinten |
| 1,489,310 A | 4/1924 | Critchlow |
| 1,526,218 A | 2/1925 | Johnson |
| 1,578,504 A | 3/1926 | Bronson et al. |
| 1,587,079 A | 6/1926 | Machino |
| 1,767,073 A | 6/1930 | Ingold |
| 1,863,360 A | 6/1932 | Weatherhead |
| 1,950,947 A | 3/1934 | Mulroyan |
| 2,023,428 A | 12/1935 | Liebhardt |
| 2,056,524 A | 10/1936 | Johnson |
| 2,066,473 A | 1/1937 | Jorgensen |
| 2,097,628 A | 11/1937 | Liebhardt |
| 2,099,335 A | 11/1937 | Hansen |
| 2,108,714 A | 2/1938 | Hirsch et al. |
| 2,116,705 A | 5/1938 | Marx et al. |
| 2,139,745 A | 12/1938 | Goodall |
| 2,147,355 A | 2/1939 | Scholtes |
| 2,159,116 A | 5/1939 | Zacharias |
| 2,211,147 A | 8/1940 | Miller |
| 2,257,321 A | 9/1941 | Arnold |
| 2,263,293 A | 11/1941 | Ewald |
| 2,264,815 A | 12/1941 | Thomsen |
| 2,340,119 A | 1/1944 | Graham |
| 2,346,445 A | 4/1944 | Merker et al. |
| 2,352,728 A | 7/1944 | Merker et al. |
| 2,429,782 A | 10/1947 | Versoy |
| 2,432,946 A | 12/1947 | Theunissen |
| 2,470,800 A | 5/1949 | Ashton |
| 2,479,499 A | 8/1949 | Le Clair |
| 2,500,720 A | 3/1950 | Van der Heem |
| 2,507,536 A | 5/1950 | Goodson |
| 2,516,583 A | 7/1950 | Moore |
| 2,535,740 A | 12/1950 | Knopp |
| 2,577,009 A | 12/1951 | Frantz |
| 2,626,974 A | 1/1953 | Howard et al. |
| 2,630,131 A | 3/1953 | Snyder |
| 2,661,018 A | 12/1953 | Snyder |
| 2,701,147 A | 2/1955 | Summerville |
| 2,722,399 A | 11/1955 | Oetiker |
| 2,753,195 A | 7/1956 | Palmer |
| 2,774,616 A | 12/1956 | Dodd et al. |
| 2,790,571 A | 4/1957 | Flaith et al. |
| 2,864,628 A | 12/1958 | Edleson |
| 2,915,325 A | 12/1959 | Foster |
| 2,926,934 A | 3/1960 | Gill |
| 2,931,668 A | 4/1960 | Baley |
| 2,937,892 A | 5/1960 | Prescott, Jr. |
| 2,948,553 A | 8/1960 | Gill et al. |
| 2,967,067 A | 1/1961 | Singer |
| 2,991,090 A | 7/1961 | De Cenzo |
| 3,017,203 A | 1/1962 | Macleod |
| 3,037,497 A | 6/1962 | Roberson |
| 3,046,028 A | 7/1962 | Nathan |
| 3,048,415 A | 8/1962 | Shook |
| 3,073,342 A | 1/1963 | Magorien |
| 3,078,068 A | 2/1963 | Romney |
| D196,473 S | 10/1963 | Hill |
| 3,124,157 A | 3/1964 | Krzewina |
| 3,129,020 A | 4/1964 | Bujnowski |
| 3,171,196 A | 3/1965 | Helitas |
| 3,191,628 A | 6/1965 | Kirkwood et al. |
| 3,217,400 A | 11/1965 | Illesy et al. |
| 3,217,771 A | 11/1965 | Beall et al. |
| 3,227,380 A | 1/1966 | Pinkston |
| 3,237,974 A | 3/1966 | Press |
| 3,245,703 A | 4/1966 | Manly |
| 3,276,799 A | 10/1966 | Moore et al. |
| 3,279,497 A | 10/1966 | Norton et al. |
| 3,314,696 A | 4/1967 | Ferguson et al. |
| 3,317,214 A | 5/1967 | Durgom |
| D209,166 S | 11/1967 | Hunt |
| D209,168 S | 11/1967 | Hunt |
| 3,352,576 A | 11/1967 | Thomas |
| 3,382,892 A | 5/1968 | Cerbin |
| 3,394,954 A | 7/1968 | Sarns |
| 3,403,930 A | 10/1968 | Bernier |
| 3,432,176 A | 3/1969 | Valenziano |
| 3,448,760 A | 6/1969 | Cranage |
| 3,450,424 A | 6/1969 | Calisher |
| 3,512,808 A | 5/1970 | Graham |
| 3,523,701 A | 8/1970 | Graham |
| 3,538,940 A | 11/1970 | Graham |
| 3,542,338 A | 11/1970 | Scaramucci |
| 3,545,490 A | 12/1970 | Burrus |
| 3,550,626 A | 12/1970 | Daniels et al. |
| 3,560,027 A | 2/1971 | Graham |
| 3,563,265 A | 2/1971 | Graham |
| 3,574,314 A | 4/1971 | Quercia |
| 3,588,149 A | 6/1971 | Demler |
| 3,596,933 A | 8/1971 | Luckenbill |
| 3,599,843 A | 8/1971 | Johnston |
| 3,600,917 A | 8/1971 | Krock |
| 3,649,050 A | 3/1972 | Woodling |
| 3,666,297 A | 5/1972 | Marks |
| 3,690,336 A | 9/1972 | Drum |
| 3,712,583 A | 1/1973 | Martindale et al. |
| 3,747,964 A | 7/1973 | Nilsen |
| 3,750,238 A | 8/1973 | Tanner |
| 3,815,887 A | 6/1974 | Curtis et al. |
| 3,817,561 A | 6/1974 | Kay |
| 3,829,135 A | 8/1974 | Forni |
| 3,876,234 A | 4/1975 | Harms |
| 3,889,710 A | 6/1975 | Brost |
| 3,899,200 A | 8/1975 | Gamble |
| 3,921,656 A | 11/1975 | Meisenheimer, Jr. et al. |
| 3,948,547 A * | 4/1976 | Gache .......................... 285/317 |
| 3,979,934 A | 9/1976 | Isenmann |
| 3,990,674 A | 11/1976 | Schattenberg |
| 4,025,049 A | 5/1977 | Schmidt |
| 4,039,213 A | 8/1977 | Walters |
| 4,072,330 A | 2/1978 | Brysch |
| 4,099,748 A | 7/1978 | Kavick |
| 4,113,627 A | 9/1978 | Leason |
| 4,116,476 A | 9/1978 | Porter et al. |
| 4,129,145 A | 12/1978 | Wynn |
| 4,142,546 A | 3/1979 | Sandau |
| D252,470 S | 7/1979 | Pawlak |
| 4,181,149 A | 1/1980 | Cox |
| 4,182,519 A | 1/1980 | Wilson |
| D254,505 S | 3/1980 | Parsons et al. |
| 4,200,605 A | 4/1980 | Imamura |
| D255,145 S | 5/1980 | Nederman |
| 4,220,360 A | 9/1980 | Jacek et al. |
| D258,526 S | 3/1981 | Nederman |
| 4,253,687 A | 3/1981 | Maples |
| D259,278 S | 5/1981 | McCaw |
| 4,271,865 A | 6/1981 | Galloway et al. |
| 4,282,175 A | 8/1981 | Volgstadt et al. |
| 4,287,644 A | 9/1981 | Durand |
| 4,294,285 A | 10/1981 | Joslyn |
| 4,296,949 A | 10/1981 | Muetterties et al. |
| 4,319,774 A | 3/1982 | Kavick |

(56) References Cited

U.S. PATENT DOCUMENTS

| | | |
|---|---|---|
| 4,330,010 A | 5/1982 | Drescher et al. |
| 4,330,142 A | 5/1982 | Paini |
| 4,331,175 A | 5/1982 | Brake et al. |
| 4,331,177 A | 5/1982 | Makishima |
| 4,340,200 A | 7/1982 | Stegmeier |
| 4,345,786 A | 8/1982 | Egert |
| 4,346,703 A | 8/1982 | Dennehey |
| 4,351,351 A | 9/1982 | Flory et al. |
| 4,366,816 A | 1/1983 | Bayard et al. |
| 4,393,548 A | 7/1983 | Herb |
| 4,397,442 A | 8/1983 | Larkin |
| 4,407,526 A | 10/1983 | Cicenas |
| 4,431,031 A | 2/1984 | Ettlinger |
| 4,431,218 A | 2/1984 | Paul |
| 4,434,121 A | 2/1984 | Schaper |
| 4,436,125 A | 3/1984 | Blenkush |
| 4,437,689 A | 3/1984 | Goebel et al. |
| 4,439,188 A | 3/1984 | Dennehey |
| 4,458,719 A | 7/1984 | Strybel |
| 4,489,914 A | 12/1984 | Stevenson et al. |
| 4,489,961 A | 12/1984 | Laidig |
| 4,500,118 A | 2/1985 | Blenkush |
| 4,527,745 A | 7/1985 | Butterfield et al. |
| 4,541,457 A | 9/1985 | Blenkush |
| 4,541,657 A | 9/1985 | Smyth |
| 4,553,587 A | 11/1985 | Traylor |
| D282,962 S | 3/1986 | Gerber |
| 4,580,816 A | 4/1986 | Campbell et al. |
| 4,603,888 A | 8/1986 | Goodall et al. |
| 4,603,890 A | 8/1986 | Huppee |
| 4,613,112 A | 9/1986 | Phlipot et al. |
| 4,616,859 A | 10/1986 | Brunet |
| 4,626,001 A | 12/1986 | Lee |
| 4,630,847 A | 12/1986 | Blenkush |
| 4,632,436 A | 12/1986 | Kimura |
| 4,635,972 A | 1/1987 | Lyall |
| 4,645,245 A | 2/1987 | Cunningham |
| 4,658,326 A | 4/1987 | Clark et al. |
| 4,659,116 A | 4/1987 | Cameron |
| 4,694,544 A | 9/1987 | Chapman |
| 4,698,027 A | 10/1987 | Vandame |
| 4,699,298 A | 10/1987 | Grant et al. |
| 4,700,926 A | 10/1987 | Hansen |
| 4,703,957 A | 11/1987 | Blenkush |
| 4,706,847 A | 11/1987 | Sankey et al. |
| 4,712,280 A | 12/1987 | Fildan |
| 4,733,890 A | 3/1988 | Vyse |
| 4,738,401 A | 4/1988 | Filicicchia |
| 4,753,268 A | 6/1988 | Palau |
| 4,768,558 A | 9/1988 | Weber |
| 4,776,067 A | 10/1988 | Sorensen |
| 4,790,567 A | 12/1988 | Kawano et al. |
| 4,790,569 A | 12/1988 | Chaffee |
| 4,792,115 A | 12/1988 | Jindra et al. |
| 4,793,637 A | 12/1988 | Laipply et al. |
| D300,361 S | 3/1989 | Tokarz |
| 4,824,148 A | 4/1989 | Grabowski |
| 4,827,921 A | 5/1989 | Rugheimer |
| 4,832,237 A | 5/1989 | Hurford, Jr. |
| 4,834,423 A | 5/1989 | DeLand |
| 4,844,512 A | 7/1989 | Gahwiler |
| 4,863,201 A | 9/1989 | Carstens |
| 4,863,202 A | 9/1989 | Oldford |
| 4,896,402 A | 1/1990 | Jansen et al. |
| 4,900,065 A | 2/1990 | Houck |
| 4,903,995 A | 2/1990 | Blenkush et al. |
| 4,923,228 A | 5/1990 | Laipply et al. |
| 4,928,859 A | 5/1990 | Krahn et al. |
| 4,928,999 A | 5/1990 | Landriault et al. |
| 4,934,655 A | 6/1990 | Blenkush et al. |
| 4,935,992 A | 6/1990 | Due |
| 4,946,200 A | 8/1990 | Blenkush et al. |
| 4,946,204 A | 8/1990 | Boticki |
| 4,949,745 A | 8/1990 | McKeon |
| 4,966,398 A | 10/1990 | Peterson |
| 4,969,879 A | 11/1990 | Lichte |
| D313,067 S | 12/1990 | Kotake et al. |
| D313,277 S | 12/1990 | Haining |
| D314,050 S | 1/1991 | Sone |
| D314,233 S | 1/1991 | Medvick |
| 4,982,736 A | 1/1991 | Schneider |
| 4,991,880 A | 2/1991 | Bernart |
| 5,009,252 A | 4/1991 | Faughn |
| 5,015,014 A | 5/1991 | Sweeney |
| 5,029,908 A | 7/1991 | Belisaire |
| 5,033,777 A | 7/1991 | Blenkush |
| D319,312 S | 8/1991 | Schneider |
| 5,052,725 A | 10/1991 | Meyer et al. |
| 5,074,601 A | 12/1991 | Spors et al. |
| 5,076,615 A | 12/1991 | Sampson |
| 5,078,429 A | 1/1992 | Braut et al. |
| 5,085,472 A | 2/1992 | Guest |
| 5,090,448 A | 2/1992 | Truchet |
| 5,090,747 A | 2/1992 | Kotake |
| 5,094,482 A | 3/1992 | Petty et al. |
| 5,104,158 A | 4/1992 | Meyer et al. |
| 5,106,127 A | 4/1992 | Briet |
| D326,155 S | 5/1992 | Boehringer et al. |
| 5,110,163 A | 5/1992 | Benson et al. |
| 5,112,084 A | 5/1992 | Washizu |
| 5,114,250 A | 5/1992 | Usui |
| D326,715 S | 6/1992 | Schmidt |
| 5,123,677 A | 6/1992 | Kreczko et al. |
| 5,143,381 A | 9/1992 | Temple |
| 5,160,177 A | 11/1992 | Washizu |
| 5,160,474 A | 11/1992 | Huff |
| 5,165,733 A | 11/1992 | Sampson |
| 5,169,161 A | 12/1992 | Jones |
| D332,482 S | 1/1993 | Petty et al. |
| 5,176,406 A | 1/1993 | Straghan |
| 5,178,303 A | 1/1993 | Blenkush et al. |
| 5,181,752 A | 1/1993 | Benson et al. |
| D333,178 S | 2/1993 | Novy |
| 5,190,224 A | 3/1993 | Hamilton |
| 5,222,279 A | 6/1993 | Frano et al. |
| 5,228,724 A | 7/1993 | Godeau |
| 5,232,020 A | 8/1993 | Mason et al. |
| D339,417 S | 9/1993 | Sampson et al. |
| 5,251,025 A | 10/1993 | Cooper et al. |
| 5,273,053 A | 12/1993 | Pohndorf |
| 5,297,826 A | 3/1994 | Percebois et al. |
| 5,316,041 A | 5/1994 | Ramacier, Jr. et al. |
| 5,318,332 A | 6/1994 | Hohmann et al. |
| 5,330,235 A | 7/1994 | Wagner et al. |
| 5,348,051 A | 9/1994 | Kallenbach |
| 5,348,354 A | 9/1994 | Badoureaux |
| 5,353,836 A | 10/1994 | deCler et al. |
| 5,356,183 A | 10/1994 | Cole |
| 5,374,088 A | 12/1994 | Moretti et al. |
| 5,385,311 A | 1/1995 | Morikawa et al. |
| 5,385,331 A | 1/1995 | Allread et al. |
| D357,307 S | 4/1995 | Ramacier, Jr. et al. |
| 5,405,333 A | 4/1995 | Richmond |
| 5,405,339 A | 4/1995 | Kohnen et al. |
| 5,405,340 A | 4/1995 | Fageol et al. |
| 5,411,300 A | 5/1995 | Mitsui |
| 5,417,442 A | 5/1995 | Jornhagen |
| 5,421,622 A | 6/1995 | Godeau |
| 5,437,650 A | 8/1995 | Larkin et al. |
| 5,440,792 A | 8/1995 | Ida |
| 5,462,313 A | 10/1995 | Rea et al. |
| 5,494,074 A | 2/1996 | Ramacier, Jr. et al. |
| D369,409 S | 4/1996 | Salter |
| 5,507,733 A | 4/1996 | Larkin et al. |
| 5,511,527 A | 4/1996 | Lorraine et al. |
| D372,093 S | 7/1996 | Sampson et al. |
| 5,536,258 A | 7/1996 | Folden |
| 5,542,712 A | 8/1996 | Klinger et al. |
| 5,547,166 A | 8/1996 | Engdahl |
| 5,547,230 A | 8/1996 | Bank et al. |
| 5,553,895 A | 9/1996 | Karl et al. |
| D375,160 S | 10/1996 | Sampson et al. |
| 5,568,946 A | 10/1996 | Jackowski |
| 5,595,217 A | 1/1997 | Gillen et al. |

(56) References Cited

U.S. PATENT DOCUMENTS

| | | |
|---|---|---|
| 5,601,317 A | 2/1997 | Crouse et al. |
| 5,607,190 A | 3/1997 | Exandier et al. |
| 5,617,609 A | 4/1997 | Bently |
| 5,620,025 A | 4/1997 | Lewin |
| 5,628,726 A | 5/1997 | Cotter |
| D380,262 S | 6/1997 | Van Funderburk et al. |
| 5,639,064 A | 6/1997 | deCler et al. |
| D382,639 S | 8/1997 | Musgrave et al. |
| D384,731 S | 10/1997 | Ramacier, Jr. et al. |
| 5,681,062 A | 10/1997 | Fukao et al. |
| 5,682,662 A | 11/1997 | Coules et al. |
| 5,683,117 A | 11/1997 | Corbett et al. |
| D387,147 S | 12/1997 | Vandermast et al. |
| 5,692,783 A | 12/1997 | Watanabe et al. |
| 5,695,223 A | 12/1997 | Boticki |
| D388,876 S | 1/1998 | Sampson |
| 5,709,244 A | 1/1998 | Patriquin et al. |
| 5,725,258 A | 3/1998 | Kujawski |
| 5,737,810 A | 4/1998 | Krauss |
| 5,745,957 A | 5/1998 | Khokhar et al. |
| 5,746,414 A | 5/1998 | Weldon et al. |
| 5,762,646 A | 6/1998 | Cotter |
| 5,784,750 A | 7/1998 | Sankovic et al. |
| 5,799,987 A | 9/1998 | Sampson |
| 5,820,614 A | 10/1998 | Erskine et al. |
| 5,837,180 A | 11/1998 | Linder et al. |
| 5,845,943 A | 12/1998 | Ramacier, Jr. et al. |
| 5,855,568 A | 1/1999 | Battiato et al. |
| 5,879,033 A | 3/1999 | Hansel et al. |
| 5,882,047 A | 3/1999 | Ostrander et al. |
| 5,884,531 A | 3/1999 | Koenig |
| D407,803 S | 4/1999 | Redman |
| 5,897,142 A | 4/1999 | Kulevsky |
| 5,911,367 A | 6/1999 | McInerney |
| 5,911,403 A | 6/1999 | deCler et al. |
| 5,911,404 A | 6/1999 | Cheng |
| 5,930,424 A | 7/1999 | Heimberger et al. |
| 5,937,501 A | 8/1999 | Imgram |
| 5,938,244 A | 8/1999 | Meyer |
| 5,941,577 A | 8/1999 | Musellec |
| 5,942,730 A | 8/1999 | Schwarz et al. |
| D413,967 S | 9/1999 | Yuen |
| 5,957,898 A | 9/1999 | Jepson et al. |
| 5,961,157 A | 10/1999 | Baron et al. |
| 5,964,485 A | 10/1999 | Hame et al. |
| 5,965,077 A | 10/1999 | Rowley et al. |
| 5,975,489 A | 11/1999 | deCler et al. |
| 5,984,378 A | 11/1999 | Ostrander et al. |
| 5,988,704 A | 11/1999 | Ryhman |
| 6,012,743 A | 1/2000 | Godeau et al. |
| 6,015,171 A | 1/2000 | Schorn |
| D419,861 S | 2/2000 | Khokhar |
| 6,019,348 A | 2/2000 | Powell |
| 6,024,124 A | 2/2000 | Braun et al. |
| 6,029,701 A | 2/2000 | Chaffardon et al. |
| 6,032,691 A | 3/2000 | Powell et al. |
| 6,041,805 A | 3/2000 | Gydesen et al. |
| D422,487 S | 4/2000 | Khokhar |
| 6,050,297 A | 4/2000 | Ostrowski et al. |
| 6,076,234 A | 6/2000 | Khokhar et al. |
| 6,077,245 A | 6/2000 | Heinrich et al. |
| 6,077,259 A | 6/2000 | Caizza et al. |
| 6,082,401 A | 7/2000 | Braun et al. |
| 6,086,044 A | 7/2000 | Guest |
| 6,089,540 A | 7/2000 | Heinrichs et al. |
| 6,099,045 A | 8/2000 | Pirona |
| 6,112,855 A | 9/2000 | Camacho et al. |
| 6,123,690 A | 9/2000 | Mejslov |
| 6,135,150 A | 10/2000 | Powell et al. |
| 6,135,992 A | 10/2000 | Wang |
| 6,142,538 A | 11/2000 | Volgstadt et al. |
| 6,145,896 A | 11/2000 | Vitel et al. |
| 6,152,914 A | 11/2000 | Van De Kerkhof et al. |
| 6,155,610 A | 12/2000 | Godeau et al. |
| 6,161,578 A | 12/2000 | Braun et al. |
| 6,176,523 B1 | 1/2001 | Winslett |
| 6,182,694 B1 | 2/2001 | Sievers et al. |
| 6,189,560 B1 | 2/2001 | Reynolds |
| 6,199,915 B1 | 3/2001 | Becker |
| 6,199,919 B1 | 3/2001 | Kawasaki et al. |
| 6,199,920 B1 | 3/2001 | Neustadtl |
| 6,206,028 B1 | 3/2001 | Holden et al. |
| 6,221,064 B1 | 4/2001 | Nadal |
| 6,231,089 B1 | 5/2001 | DeCler et al. |
| D444,054 S | 6/2001 | Bernard et al. |
| 6,250,688 B1 | 6/2001 | Kirby |
| 6,257,626 B1 | 7/2001 | Campau |
| 6,260,851 B1 | 7/2001 | Baron |
| 6,261,282 B1 | 7/2001 | Jepson et al. |
| 6,293,596 B1 | 9/2001 | Kinder |
| 6,296,508 B1 | 10/2001 | Kuwahara et al. |
| 6,296,796 B1 | 10/2001 | Gordon |
| 6,302,147 B1 | 10/2001 | Rose et al. |
| 6,318,764 B1 | 11/2001 | Trede et al. |
| 6,344,033 B1 | 2/2002 | Jepson et al. |
| 6,382,593 B1 | 5/2002 | deCler et al. |
| D459,206 S | 6/2002 | Caveney et al. |
| 6,402,207 B1 | 6/2002 | Segal et al. |
| 6,422,574 B1 | 7/2002 | Mooklar |
| 6,423,053 B1 | 7/2002 | Lee |
| 6,439,620 B1 | 8/2002 | Guest |
| 6,454,314 B1 | 9/2002 | Grosspietsch et al. |
| 6,481,758 B1 | 11/2002 | Andre et al. |
| 6,481,759 B1 | 11/2002 | Kawasaki et al. |
| 6,485,064 B1 | 11/2002 | Davidson |
| 6,485,483 B1 | 11/2002 | Fujii |
| 6,497,433 B1 | 12/2002 | Ketcham |
| 6,505,866 B1 | 1/2003 | Nakamura et al. |
| 6,508,807 B1 | 1/2003 | Peters |
| 6,520,546 B2 | 2/2003 | Szabo |
| D471,261 S | 3/2003 | Kozu |
| 6,540,263 B1 | 4/2003 | Sausner |
| 6,543,745 B1 | 4/2003 | Enerson |
| 6,595,964 B2 | 7/2003 | Finley et al. |
| 6,609,696 B2 | 8/2003 | Enerson |
| 6,612,634 B1 | 9/2003 | Zoppas |
| 6,626,419 B2 | 9/2003 | DeCler et al. |
| 6,626,465 B2 | 9/2003 | Lacroix et al. |
| D481,125 S | 10/2003 | Hayamizu |
| 6,641,177 B1 | 11/2003 | Pinciaro |
| 6,649,829 B2 | 11/2003 | Garber et al. |
| 6,652,007 B1 | 11/2003 | Hwang |
| D484,241 S | 12/2003 | Peters et al. |
| 6,669,681 B2 | 12/2003 | Jepson et al. |
| 6,676,172 B2 | 1/2004 | Alksnis |
| D486,909 S | 2/2004 | Cise et al. |
| 6,688,654 B2 | 2/2004 | Romero |
| 6,692,038 B2 | 2/2004 | Braun |
| 6,695,817 B1 | 2/2004 | Fangrow |
| 6,705,591 B2 | 3/2004 | deCler |
| 6,722,705 B2 | 4/2004 | Korkor |
| 6,722,708 B2 | 4/2004 | Morohoshi et al. |
| 6,762,365 B2 | 7/2004 | Inoue et al. |
| 6,767,017 B2 | 7/2004 | Crapart et al. |
| D495,050 S | 8/2004 | Guala |
| 6,783,520 B1 | 8/2004 | Candray et al. |
| D497,428 S | 10/2004 | Hayamizu |
| 6,799,747 B1 | 10/2004 | Lai |
| D498,533 S | 11/2004 | Hayamizu |
| 6,814,726 B1 | 11/2004 | Lauer |
| 6,840,277 B1 | 1/2005 | Nimberger |
| 6,846,021 B2 | 1/2005 | Rohde et al. |
| 6,848,602 B2 | 2/2005 | deCler et al. |
| 6,848,723 B2 | 2/2005 | Lamich |
| 6,863,314 B2 | 3/2005 | Guest |
| 6,871,669 B2 | 3/2005 | Meyer et al. |
| 6,871,878 B2 | 3/2005 | Miros |
| D503,778 S | 4/2005 | Wicks |
| 6,886,803 B2 | 5/2005 | Mikiya et al. |
| 6,897,374 B2 | 5/2005 | Garber et al. |
| 6,899,315 B2 | 5/2005 | Maiville et al. |
| 6,902,144 B2 | 6/2005 | deCler |
| D507,647 S | 7/2005 | Beck et al. |
| 6,916,007 B2 | 7/2005 | deCler et al. |

(56) References Cited

U.S. PATENT DOCUMENTS

| | | |
|---|---|---|
| 6,916,050 B2 | 7/2005 | Milhas |
| 6,926,311 B2 | 8/2005 | Chang et al. |
| 6,929,246 B2 | 8/2005 | Arzenton et al. |
| 6,945,273 B2 | 9/2005 | Reid |
| 6,949,084 B2 | 9/2005 | Marggi et al. |
| 6,962,275 B2 | 11/2005 | deCler et al. |
| 6,978,800 B2 | 12/2005 | deCler et al. |
| 6,981,547 B2 | 1/2006 | Maguire et al. |
| 6,997,486 B2 | 2/2006 | Milhas |
| 6,997,919 B2 | 2/2006 | Olsen et al. |
| 7,005,581 B2 | 2/2006 | Burnette |
| 7,011,342 B2 | 3/2006 | Guivarc'h et al. |
| 7,014,214 B2 | 3/2006 | Kaneko |
| D522,109 S | 5/2006 | White et al. |
| 7,040,670 B2 | 5/2006 | Madden |
| 7,044,161 B2 | 5/2006 | Tiberghien |
| 7,044,506 B2 | 5/2006 | Dong |
| D523,553 S | 6/2006 | Beck et al. |
| 7,080,665 B2 | 7/2006 | Whall |
| 7,081,223 B2 | 7/2006 | Khoury |
| 7,108,297 B2 | 9/2006 | Takayanagi et al. |
| 7,118,138 B1 | 10/2006 | Rowley et al. |
| 7,128,348 B2 | 10/2006 | Kawamura et al. |
| 7,137,654 B2 | 11/2006 | Segal et al. |
| 7,140,592 B2 | 11/2006 | Phillips |
| 7,147,252 B2 | 12/2006 | Teuscher et al. |
| 7,150,478 B2 | 12/2006 | Poirier et al. |
| 7,153,296 B2 | 12/2006 | Mitchell |
| 7,163,022 B2 | 1/2007 | Whall |
| D540,944 S | 4/2007 | Guala |
| 7,210,917 B2 | 5/2007 | Lai et al. |
| D547,446 S | 7/2007 | Racz et al. |
| D550,355 S | 9/2007 | Racz et al. |
| D557,409 S | 12/2007 | Veliss et al. |
| 7,316,428 B2 | 1/2008 | Takayanagi et al. |
| D564,660 S | 3/2008 | Hayashi |
| 7,343,931 B2 | 3/2008 | Packham |
| D567,340 S | 4/2008 | Tiberghien |
| 7,352,771 B2 | 4/2008 | Garber |
| D569,507 S | 5/2008 | Blanchard |
| D569,955 S | 5/2008 | Chen |
| 7,377,553 B2 | 5/2008 | Takayanagi |
| D570,457 S | 6/2008 | Brown |
| 7,390,029 B2 | 6/2008 | Matsubara |
| 7,394,375 B2 | 7/2008 | Johnson |
| 7,434,842 B2 | 10/2008 | Schmidt |
| 7,434,846 B2 | 10/2008 | Baumgartner |
| 7,448,653 B2 | 11/2008 | Jensen et al. |
| 7,464,970 B2 | 12/2008 | Yamada et al. |
| 7,467,813 B2 | 12/2008 | Gunderson |
| 7,469,472 B2 | 12/2008 | DeCler et al. |
| 7,478,840 B2 | 1/2009 | Youssefifar |
| 7,488,446 B2 | 2/2009 | Meyer et al. |
| 7,494,156 B2 | 2/2009 | Okada |
| 7,503,595 B2 | 3/2009 | McKay |
| 7,516,990 B2 | 4/2009 | Jamison et al. |
| 7,546,857 B2 | 6/2009 | Chadbourne et al. |
| 7,547,047 B2 | 6/2009 | deCler et al. |
| D595,845 S | 7/2009 | Miros et al. |
| D595,846 S | 7/2009 | Racz et al. |
| D596,288 S | 7/2009 | Racz et al. |
| D596,739 S | 7/2009 | Ng et al. |
| 7,562,906 B2 | 7/2009 | Schmidt |
| 7,566,077 B2 | 7/2009 | Tsurumi |
| 7,581,763 B2 | 9/2009 | Salomon-Bahls |
| D602,128 S | 10/2009 | Williams et al. |
| 7,614,666 B2 | 11/2009 | Eggert et al. |
| 7,631,660 B2 | 12/2009 | deCler et al. |
| 7,647,954 B2 | 1/2010 | Garber et al. |
| 7,666,178 B2 | 2/2010 | McMichael |
| D612,019 S | 3/2010 | Williams et al. |
| D612,021 S | 3/2010 | Schmidt |
| 7,677,608 B2 | 3/2010 | Takayanagi |
| D613,853 S | 4/2010 | Ng et al. |
| 7,695,020 B2 | 4/2010 | Schmidt |
| 7,708,025 B2 | 5/2010 | Johnson |
| 7,731,244 B2 | 6/2010 | Miros et al. |
| D619,706 S | 7/2010 | Schon et al. |
| 7,770,939 B2 | 8/2010 | Jensen et al. |
| 7,806,139 B2 | 10/2010 | Packham et al. |
| 7,841,357 B2 | 11/2010 | Rankin |
| D629,894 S | 12/2010 | Lombardi, III et al. |
| 7,849,877 B2 | 12/2010 | Tan et al. |
| D630,320 S | 1/2011 | Lombardi, III et al. |
| D632,783 S | 2/2011 | Maesarapu |
| 7,878,553 B2 | 2/2011 | Wicks et al. |
| D634,840 S | 3/2011 | Lombardi, III et al. |
| D639,398 S | 6/2011 | Wilhelm |
| 7,954,374 B2 | 6/2011 | Rankin |
| 7,954,515 B2 | 6/2011 | Gerst |
| D642,244 S | 7/2011 | Wilhelm |
| 7,976,071 B2 | 7/2011 | Bibby |
| D645,547 S | 9/2011 | Lombardi, III et al. |
| D649,240 S | 11/2011 | Lewis et al. |
| D650,478 S | 12/2011 | Lewis |
| D652,510 S | 1/2012 | Lombardi, III et al. |
| D652,511 S | 1/2012 | Lombardi, III et al. |
| D654,573 S | 2/2012 | Lombardi, III et al. |
| 8,113,546 B2 | 2/2012 | Jensen et al. |
| D655,393 S | 3/2012 | Whitaker |
| D663,022 S | 7/2012 | Lombardi, III et al. |
| 8,235,426 B2 | 8/2012 | Pisula, Jr. et al. |
| 2001/0017466 A1 | 8/2001 | Braun |
| 2002/0022762 A1 | 2/2002 | Beane et al. |
| 2002/0070547 A1 | 6/2002 | Guertin |
| 2002/0093192 A1 | 7/2002 | Matkovich |
| 2002/0140172 A1 | 10/2002 | Platusich |
| 2002/0156344 A1 | 10/2002 | Pasricha et al. |
| 2002/0185861 A1 | 12/2002 | Inoue |
| 2003/0004397 A1 | 1/2003 | Kameya et al. |
| 2003/0067162 A1 | 4/2003 | Welsh et al. |
| 2003/0193188 A1 | 10/2003 | Miros |
| 2003/0230894 A1 | 12/2003 | Cleveland et al. |
| 2004/0021318 A1 | 2/2004 | Fritze et al. |
| 2004/0056484 A1 | 3/2004 | Kwon et al. |
| 2004/0094903 A1 | 5/2004 | Sutherland |
| 2004/0195830 A1 | 10/2004 | Gilmour |
| 2004/0199143 A1 | 10/2004 | Lauer |
| 2004/0227346 A1 | 11/2004 | Jamison et al. |
| 2004/0232696 A1 | 11/2004 | Andre |
| 2005/0033237 A1 | 2/2005 | Fentress et al. |
| 2005/0046184 A1 | 3/2005 | Chang |
| 2005/0057042 A1 | 3/2005 | Wicks |
| 2005/0082828 A1 | 4/2005 | Wicks et al. |
| 2005/0087981 A1 | 4/2005 | Yamada et al. |
| 2005/0209583 A1 | 9/2005 | Powers et al. |
| 2005/0217265 A1 | 10/2005 | Popp et al. |
| 2005/0242579 A1 | 11/2005 | Bright et al. |
| 2005/0275220 A1 | 12/2005 | Shu |
| 2006/0066100 A1 | 3/2006 | Nakashima et al. |
| 2006/0128180 A1* | 6/2006 | Gammons ............... 439/76.1 |
| 2006/0152003 A1 | 7/2006 | Slunick et al. |
| 2006/0202146 A1 | 9/2006 | Doyle |
| 2006/0264814 A1 | 11/2006 | Sage |
| 2006/0293629 A1 | 12/2006 | Cote, Sr. et al. |
| 2007/0025811 A1 | 2/2007 | Wilhelm |
| 2007/0029795 A1 | 2/2007 | Moner et al. |
| 2007/0029796 A1 | 2/2007 | Bibby |
| 2007/0106213 A1 | 5/2007 | Spera et al. |
| 2007/0137718 A1 | 6/2007 | Rushlander et al. |
| 2007/0169825 A1 | 7/2007 | Packham et al. |
| 2007/0209716 A1 | 9/2007 | Rankin |
| 2007/0284875 A1 | 12/2007 | Salomon-Bahls et al. |
| 2008/0007051 A1 | 1/2008 | Jensen et al. |
| 2008/0011703 A1 | 1/2008 | Schmeisser et al. |
| 2008/0012314 A1 | 1/2008 | Harger et al. |
| 2008/0018105 A1 | 1/2008 | Le Bars |
| 2008/0048442 A1* | 2/2008 | Kerin et al. ............. 285/305 |
| 2008/0048448 A1 | 2/2008 | Jamison et al. |
| 2008/0078464 A1 | 4/2008 | Loewe |
| 2008/0111371 A1 | 5/2008 | Feger et al. |
| 2008/0111372 A1 | 5/2008 | Trede et al. |
| 2008/0129047 A1 | 6/2008 | Blivet et al. |
| 2008/0164694 A1 | 7/2008 | Zdroik et al. |

(56) References Cited

U.S. PATENT DOCUMENTS

| | | |
|---|---|---|
| 2008/0191466 A1 | 8/2008 | Knipple et al. |
| 2008/0200901 A1 | 8/2008 | Rasmussen et al. |
| 2008/0277923 A1 | 11/2008 | Brandt et al. |
| 2008/0277924 A1 | 11/2008 | Jensen et al. |
| 2008/0284167 A1 | 11/2008 | Lim et al. |
| 2008/0287920 A1 | 11/2008 | Fangrow et al. |
| 2009/0079187 A1 | 3/2009 | Malone |
| 2009/0127847 A1 | 5/2009 | Hagen et al. |
| 2009/0129047 A1 | 5/2009 | Park et al. |
| 2009/0140519 A1 | 6/2009 | Pavnaskar et al. |
| 2009/0167018 A1 | 7/2009 | Lien |
| 2009/0187166 A1 | 7/2009 | Young |
| 2009/0188575 A1 | 7/2009 | Williams et al. |
| 2009/0256355 A1 | 10/2009 | Wicks et al. |
| 2010/0001516 A1 | 1/2010 | Pisula, Jr. et al. |
| 2010/0056975 A1 | 3/2010 | Dale et al. |
| 2010/0078934 A1 | 4/2010 | Matsunaga |
| 2010/0185040 A1 | 7/2010 | Uber et al. |
| 2010/0194100 A1 | 8/2010 | Koch |
| 2010/0276922 A1 | 11/2010 | Rehder et al. |
| 2010/0295295 A1 | 11/2010 | Schmidt |
| 2010/0301599 A1 | 12/2010 | Jensen et al. |
| 2010/0319796 A1 | 12/2010 | Whitaker |
| 2011/0012340 A1 | 1/2011 | Packham et al. |
| 2011/0127767 A1 | 6/2011 | Wicks et al. |
| 2011/0204621 A1 | 8/2011 | Whitaker et al. |
| 2011/0204622 A1 | 8/2011 | Lewis et al. |
| 2011/0210541 A1 | 9/2011 | Lewis et al. |
| 2012/0031515 A1 | 2/2012 | Whitaker |
| 2012/0068457 A1 | 3/2012 | Pisula, Jr. et al. |

FOREIGN PATENT DOCUMENTS

| | | |
|---|---|---|
| CN | 201170406 | 12/2008 |
| DE | 1868896 | 3/1963 |
| DE | 3439522 | 8/1985 |
| DE | 3533000 | 3/1987 |
| DE | 4122455 | 1/1993 |
| DE | 19800050 | 7/1998 |
| DE | 102005015343 | 10/2006 |
| EP | 0360634 | 3/1990 |
| EP | 0390746 | 10/1990 |
| EP | 0267067 | 7/1991 |
| EP | 0482277 | 4/1992 |
| EP | 0592823 | 4/1994 |
| EP | 0715111 | 6/1996 |
| EP | 0865779 | 9/1998 |
| EP | 0877891 | 11/1998 |
| EP | 0890054 | 1/1999 |
| EP | 0982525 | 3/2000 |
| EP | 1497582 | 1/2005 |
| EP | 1564469 | 8/2005 |
| EP | 1843074 | 10/2007 |
| FR | 2031965 | 11/1970 |
| FR | 2429370 | 1/1980 |
| FR | 280871 | 10/2001 |
| FR | 2853043 | 10/2004 |
| FR | 2870921 | 12/2005 |
| FR | 2903164 | 1/2008 |
| GB | 583459 | 12/1946 |
| GB | 890775 | 3/1962 |
| GB | 2177769 | 1/1987 |
| GB | 2218166 | 11/1989 |
| GB | 2271157 | 4/1994 |
| GB | 2379253 | 3/2003 |
| JP | 53-006918 | 1/1978 |
| JP | 5-223189 | 8/1993 |
| JP | 7-145889 | 6/1995 |
| JP | 10-169869 | 6/1998 |
| JP | 11-82849 | 3/1999 |
| JP | 2003-42363 | 2/2003 |
| JP | 2003-42368 | 2/2003 |
| JP | 6-512540 | 4/2006 |
| WO | WO 93/17270 | 9/1993 |
| WO | WO 95/08732 | 3/1995 |
| WO | WO 00/79172 | 12/2000 |
| WO | WO 2004/027269 | 4/2004 |
| WO | WO 2004/104466 | 12/2004 |
| WO | WO 2005/064216 | 7/2005 |
| WO | WO 2006/031958 | 3/2006 |
| WO | WO 2006/073778 | 7/2006 |
| WO | WO 2006/084171 | 8/2006 |
| WO | WO 2006/135666 | 12/2006 |
| WO | WO 2007/038222 | 4/2007 |
| WO | WO 2007/116387 | 10/2007 |
| WO | WO 2007/120620 | 10/2007 |
| WO | WO 2008/023021 | 2/2008 |
| WO | WO 2009/026441 | 2/2009 |

OTHER PUBLICATIONS

Barbed Tee Adapter, 1/2 in to 2/8 in to 1/2 in [Item # F1728], http://www.horticulturesource.com/product_info.php/products_id/4016/language/en; dated accessed Sep. 14, 2009, 3 pages.

Capabilities [online], Jay Manufacturing Corp., retrieved on Apr. 9, 2010, retrieved from the Internet: <URL: http://www.jaymfg.com/capabilities.htm>, 2 pages.

Flojet "Quick Connect" Port System Adapter 90 Elbow Type Quad Port X 1/2" Hose Barb, http://www.amazon.com/Quick-Connect-Port-System-Quad-Barb-90/dp/B0000AZ771/ref=sr_1_16?s=sporting-goods&ie=UTF8&qid=1300220596&sr=1-16, date accessed Sep. 14, 2009; 3 pages.

High-Flow Quick Disconnect Couplings; http://www.coleparmer.com/catalog/product_view.asp?sku=3130355; date accessed Sep. 14, 2009, 3 pages.

Mills, The Process of Vacuum-forming Plastic Parts, IPFrontline.com [online], retrieved on Apr. 9, 2010, retrieved from the Internet: <URL: http://www.ipfrontline.com/depts/article.asp?id=453&deptid=2>, 3 pages.

Nylon, Polypropylene Kynar (PVDF) Plastic Fittings for Flexible Tubing & Hose, http://www.omega.com/pdf/tubing/fittings_tubing_hose/nylon_poly_kynar/nylon.asp; dated accessed Sep. 14, 2009, 2 pages.

Science of Hose Barbs, Colder Products Company, http://www.pddnet.com/article-the-science-of-hose-barbs/, date accessed Sep. 4, 2009, 6 pages.

Stackable Hose Barb Elbow—1/2" CTS × 1/2 ID Barb, http://www.freshwatersystems.com/p-1714-stackable-hose-barb-elbow-12-cts-x-12-id-barb.aspx?affiliatied=10052&utm_source=shopzilla&utm_medium=Feed&utm_campaign=Product&utm_term=3512-1008, date accessed Sep. 14, 2009, 1 page.

Stainless Steel Overview: History [online], Stainless Steel Industry of North America, retrieved on Apr. 9, 2010, retrieved from the Internet: <URL: http://www.ssina.com/overview/history.html>, 1 page.

Singapore Examination Report mailed Jul. 3, 2014 for Singapore Patent Application No. 201204718-9, 5 pages.

* cited by examiner

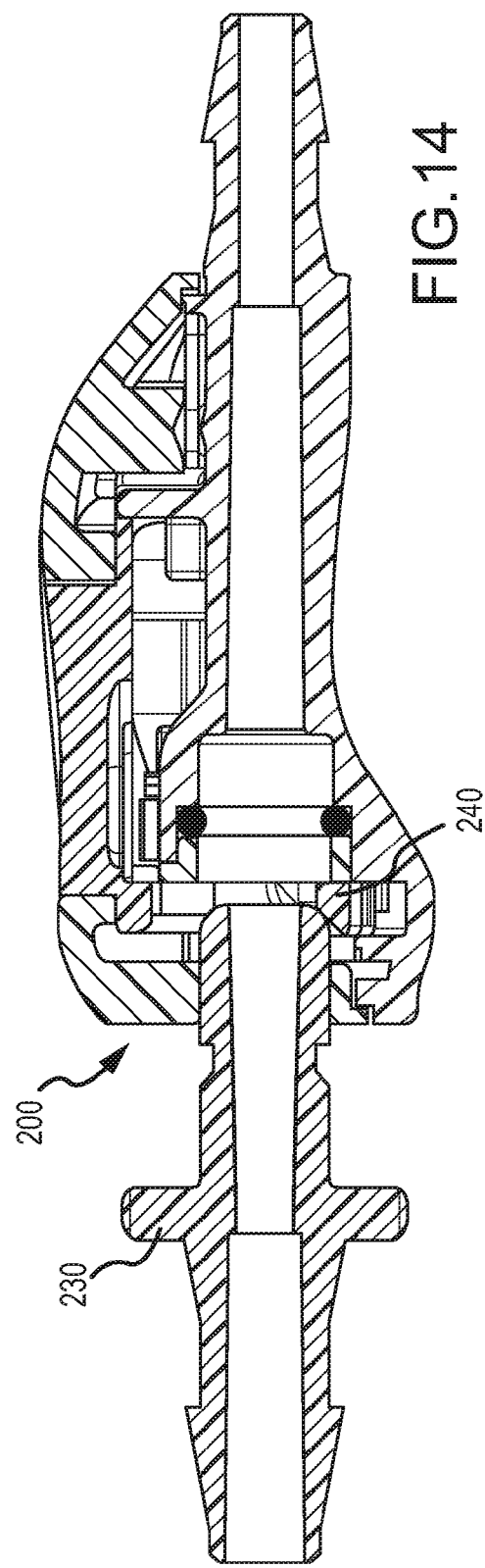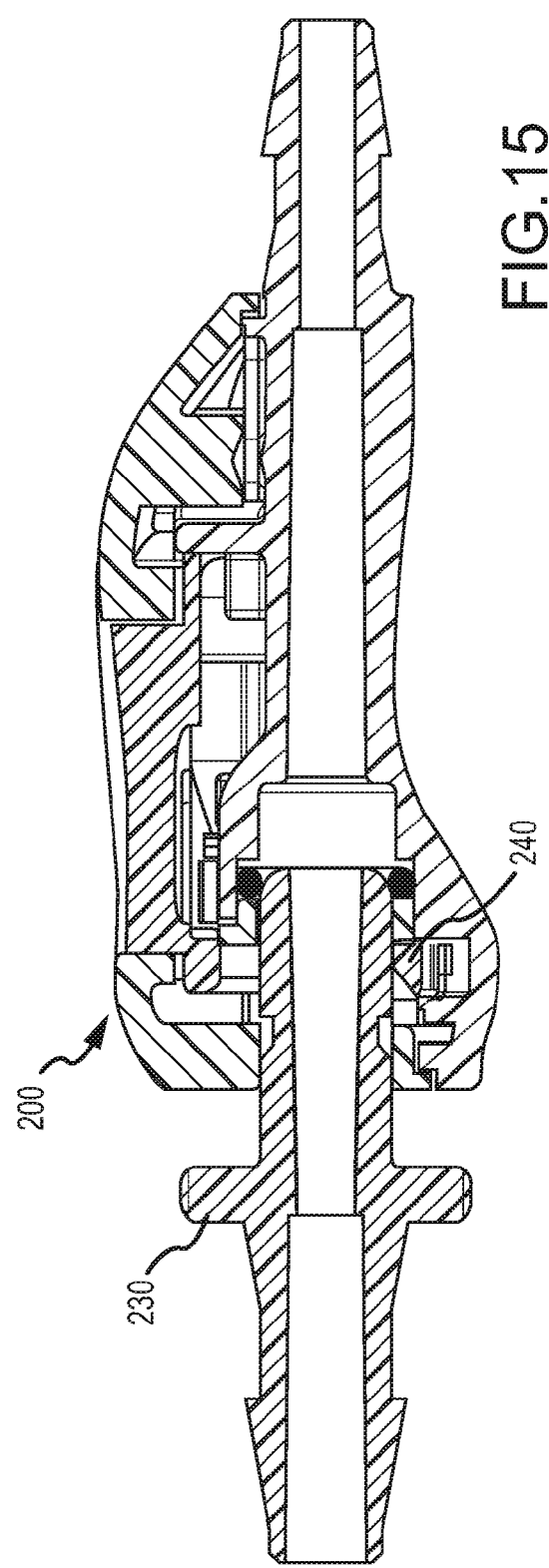

FLUID CONNECTOR LATCHES WITH PROFILE LEAD-INS

CROSS REFERENCE TO RELATED APPLICATIONS

This application claims the benefit of priority pursuant to 35 U.S.C. §119(e) of U.S. provisional application No. 61/361,306 filed 2 Jul. 2010 entitled "Fluid connector latches with profile lead-ins" and U.S. provisional application No. 61/289,990 filed 23 Dec. 2009 entitled "Fluid connector latches with profile lead-ins" each of which is hereby incorporated herein by reference in its entirety.

The present application is related to U.S. patent application Ser. No. 12/976,943 filed 22 Dec. 2010 entitled "Button latch with integrally molded cantilever springs"; U.S. patent application Ser. No. 12/976,921 filed 22 Dec. 2010 entitled "Male bayonet connector"; U.S. design patent application Ser. No. 29/352,637 filed 23 Dec. 2009 entitled "Female dual lumen connector"; and U.S. design patent application Ser. No. 29/351,665 filed 9 Dec. 2009 entitled "Male dual lumen bayonet connector," each of which is hereby incorporated herein by reference in its entirety.

BACKGROUND

1. Technical Field

The present disclosure relates generally to the field of both gaseous and liquid fluid transport and more specifically, to a connector for creating a releasable fluid seal connection between one or more sections of tubing and a female latch.

2. Description of Related Art

Tubing sections are often joined together to provide for gas and/or liquid fluid flow from one component to another. Thus, it is often desirable to connect and disconnect tubing sections from one another. For example, when a patient's blood pressure is taken with an automatic blood pressure monitor, tubing from the blood pressure cuff (which is generally wrapped around the patient's arm) is connected to the tubing that is connected to the blood pressure monitor. To disconnect the cuff from the blood pressure monitor, it is desirable to merely detach the tubing section connected to the cuff from the tubing connected to the blood pressure monitor. Similarly, when providing intravenous fluids, it is often required to replace an empty fluid bag with a full fluid bag without removing the intravenous needle or stent from the patient. In order to switch between the first fluid bag and the second fluid bag, it is desirable to merely detach a tubing section connected with the fluid bag to the tubing section connected with the needle or stent placed intravenously in the patient, which can then be easily connected with a tubing section connected with the new fluid bag.

Existing tubing connectors are prone to leakage and unwanted disconnection when the patient is still receiving treatment via the connected tubes due to side loads caused by the weight of the connected tubes and components, as well as accidental pulling of the tubes by the patient or medical personnel.

Furthermore, certain medical devices require the use of multiple tubes for supplying fluid between the patient and the device. For example, certain models of blood pressure monitors, such as the Dinamap Procare series, manufactured by General Electric, employ dual tubes for connecting the blood pressure cuff to the monitor. As such, a connector including multiple air passages for directing airflow between the tube segments is desirable, so as to avoid having to individually connect and disconnect multiple connectors when hooking or unhooking a patient to the monitor.

From the foregoing, it can be appreciated that a need exists for an improved bayonet connector that may connect one or more sections of tubing to create a gas and/or liquid fluid seal that cooperates with a female receiving connector to provide a more resilient connection and maintain a fluid-tight seal when the male bayonet connector is placed under axial tension or side load forces.

The information included in this Background section of the specification, including any references cited herein and any description or discussion thereof, is included for technical reference purposes only and is not to be regarded subject matter by which the scope of the invention is to be bound.

SUMMARY

Improved female tube connectors are disclosed herein that reduce insertion force requirements for coupling with male connectors. Additionally, the female tube connectors increase the amount of force required to extract male connectors once they are secured within the female tube connectors to prevent accidental uncoupling of the male connector from the female connector.

Generally, a locking member that is coupled to a button of the female tube connectors may take various forms to help ensure relatively low insertion force and relatively high extraction force for coupling and uncoupling male connectors. Specifically, the locking member may include a profile lead-in to help reduce the amount of force to insert a male connector into the female connector while increasing the amount of force to extract the male connector once coupled to the female connector.

In one embodiment, a female receiving connector for connecting sections of tubing is provided. The female receiving connector includes a housing having a top housing portion and a bottom housing portion coupled to the top housing portion. The female receiving connector also includes a button moveably coupled within the housing. A locking plate is integral with or coupled to the button and configured to move with the button. The locking plate has a profile lead-in having an interfacing surface located at a proximal side of the profile lead-in for interfacing with a male connector. The interfacing surface extends along at least a portion of at of a circumferential edge of an aperture formed within the locking plate and is tapered along the portion of the circumferential edge. Additionally, the profile lead-in includes a locking surface located at a distal side of the lofted lead-in for securing the male connector within the housing of the female receiving connector. A substantially flat surface is located between the interfacing surface and the locking surface.

In another embodiment, a female receiving connector for transporting fluids is provided. The female receiving connector includes a housing defining at least one lumen for fluid flow. The housing includes a top housing portion, a bottom housing portion coupled to the top housing portion and a button moveably coupled within the housing. Additionally, the female receiving connector includes a locking member coupled to the button and configured to displace with the button when force is applied to the button or to a surface of the locking member. The locking plate has a profile lead-in. The profile lead-in includes a curved surface located at a proximal side of the profile lead-in for interfacing with a male connector and a locking surface located at a distal side of the profile lead-in for securing the male connector within the housing of the female receiving connector. A substantially flat surface is located between the curved surface and the locking surface and the curved surface extends from a proximal face of the locking member to the substantially flat surface.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE DRAWINGS

FIG. 14 is a cross sectional view of the dual lumen female connector of FIG. 10 with the dual lumen male connector contacting a profile lead-in.

FIG. 15 is a cross-sectional view of the dual lumen male bayonet connector passing through the aperture of FIG. 12.

DETAILED DESCRIPTION

Embodiments of female receiving connectors in conjunction with male bayonet connectors, may be used to releasably connect sections of tubing. In one embodiment, the female receiving connector includes a latch plate with a profile lead-in that extends upward along the lateral sides of the aperture in the latch plate. The profile lead-in provides extended latching surfaces for the latch plate to secure a male bayonet connector. When the male bayonet connector is inserted into the female receiving connector, a distal end of the male bayonet connector interfaces the profile lead-in, biases the latch plate downward, and lowers a receiving aperture through which the male bayonet connector may pass. The male bayonet connector includes an annular channel that is engaged by the profile lead-in upon sufficient insertion of the male bayonet connector into the female receiving connector.

The orientations "proximal" and "distal" as used herein have been arbitrarily chosen, and are not meant to limit the present disclosure, but will follow the convention just described with reference to the ends of the female receiving connector 206 and male dual bayonet connector 102.

In an alternative embodiment, a female receiving connector may include a locking plate having a profile lead-in as a curved bottom surface of the aperture in the locking plate. When the male bayonet connector is inserted into the female connector, the male bayonet connector interfaces the profile lead-in, biasing the locking plate downward and lowering a receiving aperture through which the male bayonet connector may pass. The male bayonet connector's annular channels are engaged by a distal surface of the profile lead-in upon sufficient insertion of the male bayonet connector into the female receiving connector.

In some embodiments, the profile lead-in lead-in may be implemented in multiple parallel lumen configurations. For example, in some embodiments, the profile lead-in may be implemented in a dual lumen configuration (e.g., the female connector having two parallel lumens through which fluid may pass and into which male connectors may be inserted). Additionally, in some embodiments, the profile lead-in may have one or more chamfered surfaces that engage the annular channels of the male bayonet connectors. In some embodiments, a distal edge of the locking plate may be flat to interface with the flat surface of the annular channel.

Figure 1:
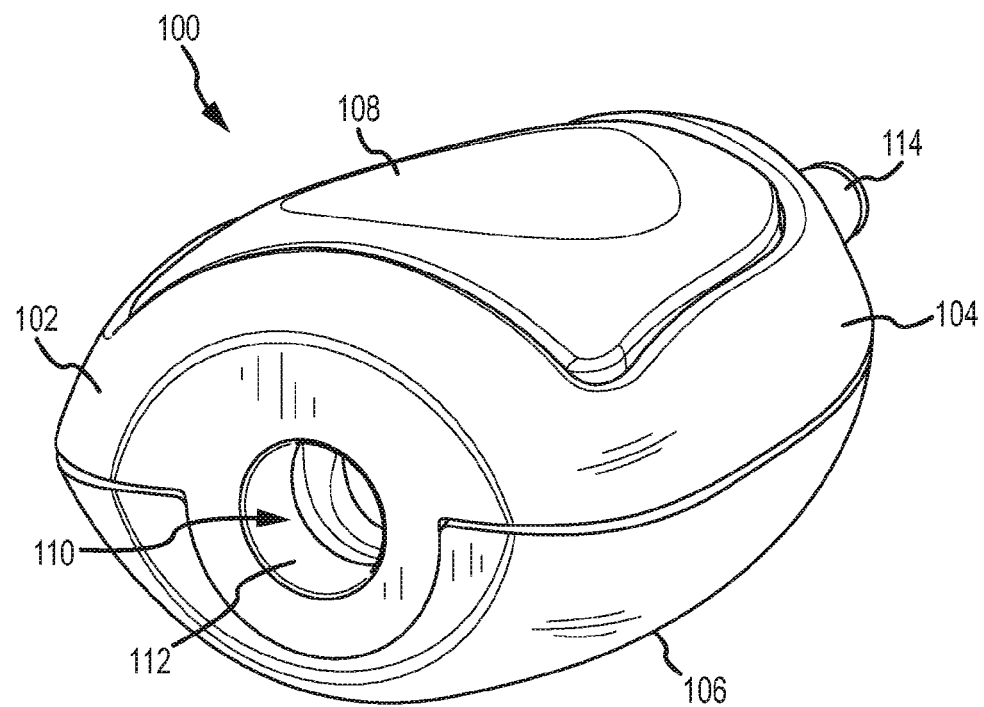
FIG. 1 illustrates a female receiving connector in accordance with an exemplary embodiment.

An exemplary female receiving connector 100 is illustrated in FIG. 1. The female receiving connector 100 includes a housing 102 having a top portion 104 and a bottom portion 106. A button 108 is movably coupled to the housing 102 and externally accessible to allow for disengagement of a male connector from a locking member, as discussed in greater detail below. The housing 102 and button 108 may be made of a suitable material via a suitable process. In some embodiments, the housing 102 and button 108 may be made of a plastic material via a molding process, such as an injection molding process. In other embodiments, one or more parts of the female receiving connector 100 may be made via a milling process, such as a computer numerical control (CNC) milling process. The top portion 104 and the bottom portion 106 may be secured together in a suitable manner, such as implementing snap fits that are integrally formed with the top and bottom portions. In other embodiments, the top and bottom portions may be secured together in other manners, for example, via adhesive or ultrasonic welding.

The housing 102 includes receiving aperture 110 through which a male bayonet connector may be inserted. The aperture 110 is located at a proximal end of the female receiving connector 100 and may be defined by the upper and/or lower portions 102, 106 of the housing 102. The aperture 110 constitutes a proximal end of lumen 112 extending through the female receiving connector 100. The lumen 112 continues through a barbed tube connector 114 located at the distal end of the female receiving connector 100. The barbed tube connector 114 is configured for attachment of plastic tubing.

Figure 2:
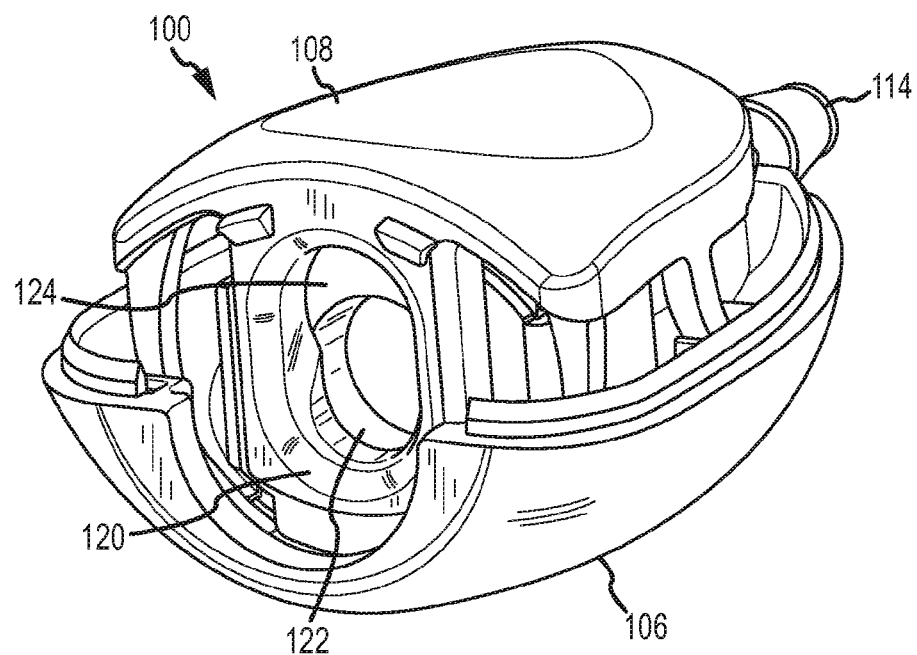
FIG. 2 illustrates the female receiving connector of FIG. 1 without a top housing portion.

FIG. 2 shows the female receiving connector 100 with the top portion 104 of the housing 102 removed to show additional details inside the housing 102. As illustrated, the button 108 includes a locking plate 120. In some embodiments, the locking plate 120 may be integrally formed with the button 108, while in other embodiments, the locking plate 120 and the button 108 may be formed separately and later coupled together. Further, in other embodiments structures other than a button, e.g., a slide, a switch, a lever, or other structures, may be used to operate the locking plate 120. The locking plate 120 extends downward from the button 108 and is configured to move in conjunction with the button 108. A sealing member 122, such as a rubber O-ring may be located directly behind the locking member 120. The sealing member 122 is secured in place behind the locking plate 120 by a sealing member retainer 124. The sealing member retainer 124 may be a suitable holding structure into which the sealing member 122 is inserted and held. In some embodiments, the sealing member retainer 124 may be integrally formed with the bottom portion 106 of the housing 102. In other embodiments, the sealing member retainer 124 may be formed separately from the bottom portion 106 of the housing 102 and subsequently coupled to the bottom portion. The sealing member 122 may be secured within a channel located behind the sealing member retainer 124.

Figure 3:
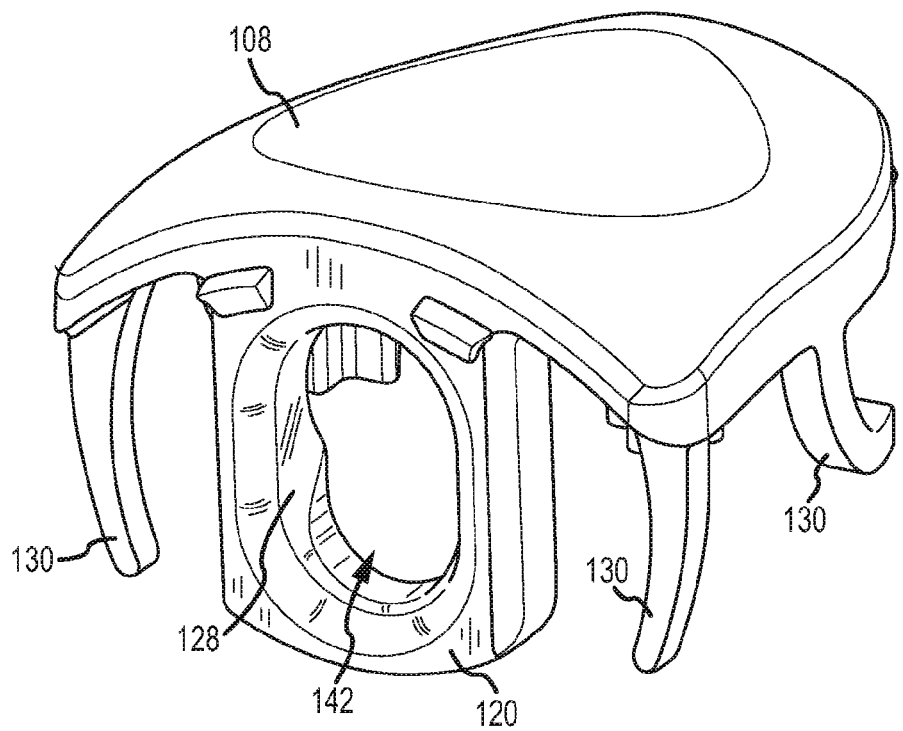
FIG. 3 illustrates a button of the female receiving connector of FIG. 1 having a locking plate with profile lead-ins.

The locking plate 120 includes a profile lead-in 128. FIG. 3 illustrates the button 108 independent from the bottom portion 106 of the housing 102, so that the profile lead-in 128 may be more easily seen and described. Generally, the profile lead-in 128 extends upward along edges 140 of an aperture 142 of the locking plate 120. The profile lead-in 128 functions as an improved locking structure. That is, because it extends upward along the edges of the aperture 142, the profile lead-in 128 provides additional structure for locking in a male bayonet connector.

As illustrated, the button 108 includes the locking member 120 as an integrated part. Additionally, the button 108 includes curved legs 130 which may interface with the bottom portion 106 of the housing 102 and function as springs to hold the button 108 up within the housing 102. That is, the legs 130 have a normally extended position to hold up the button 108. When the button is pressed, the legs 130 may bend and when pressure is released, the legs may return to full extension, thus providing a spring function. In other embodiments, other kinds of mechanical action than springs may be employed to raise the button back up to its resting place when the force is removed.

Figure 4:
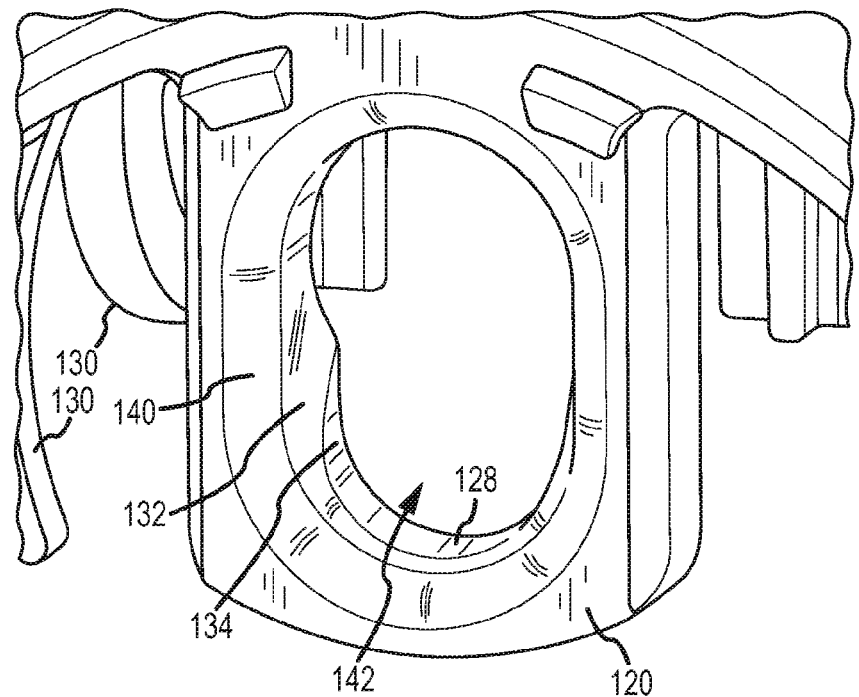
FIG. 4 is an enlarged view of the locking plate with profile lead-ins of FIG. 3.

FIG. 4 is an enlarged image of the aperture 142 of the button 108 shown in FIG. 3. As may be seen, the profile lead-in 128 has a ramped shape. Specifically, a proximal or interfacing surface 132 of the profile lead-in 128 tapers toward the distal edge 134 of the locking plate 120 as the profile lead-in 128 progress upward along the edge 140 of the aperture 142. The ramp is provided so that as a male bayonet connector is pressed against the profile lead-in 128, for example, during insertion of the male bayonet connector into the female receiving connector 100, the locking plate 120 is forced downward. The range of angles for the pitch of the ramp depends on the distance the groove is from the front of the male connector tip or the distance the male connector has to travel in order for the profile lead in to lock into the groove on the male connector. In some embodiments, the ramp may be pitched at between 44° and 46°.

Figure 5:
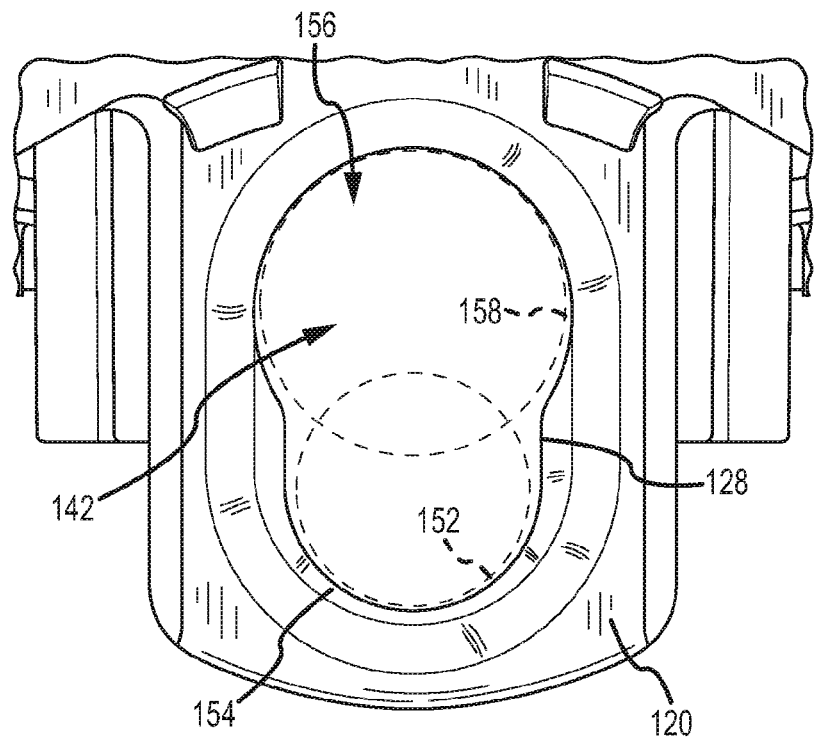
FIG. 5 is a front elevation view of the locking plate of FIG. 3 illustrating an aperture of the locking plate.

FIG. 5 shows the aperture 142 as including two generally circular areas with overlapping circumferences. A first area 150 is defined by a first circumference 152 in a lower portion of the aperture 142. The profile lead-in 128 and a base lead-in 154 define the circumference 152 of the first area 150. A second area 156 is defined by a second circumference 158. A portion of the second circumference 158 may be formed by a top edge of the profile lead-in 128. As such, the top edge of the profile lead-in 128 may have a curved shape.

The second circumference 158 and the first circumference 152 overlap. The second circumference 158 is larger than the first circumference 152 and, therefore, the second area 156 is larger than the first area 150. The second area 158 is large enough to allow for the passage of a male bayonet therethrough, while the first area 152 functions as a locking aperture to engage and hold the male bayonet connector.

Figure 6:
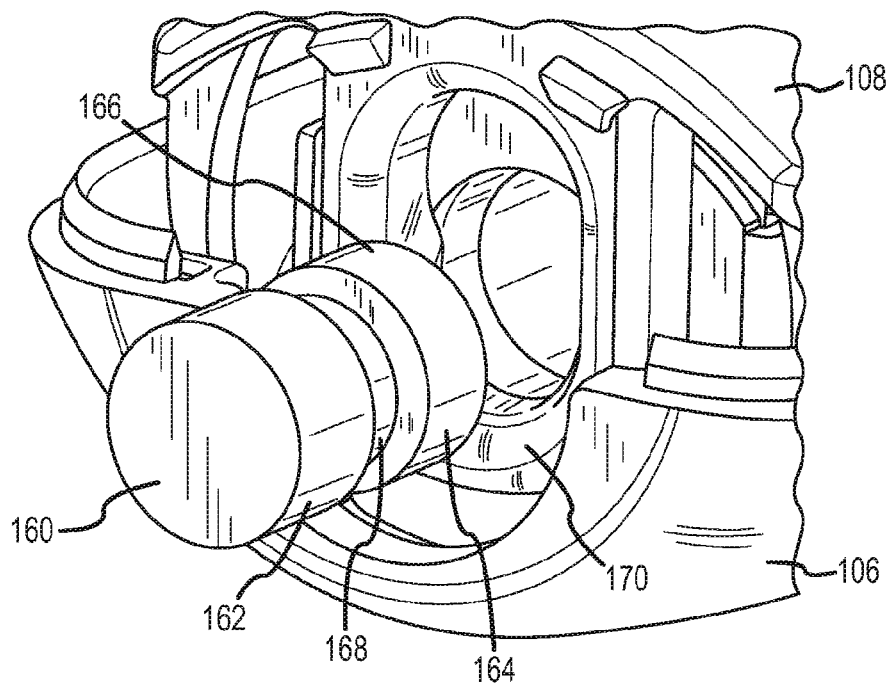
FIG. 6 illustrates a male bayonet connector entering a housing of the female receiving connector of FIG. 2.

FIG. 6 illustrates a male bayonet connector 160 entering the aperture of the housing 102. In some embodiments, the male bayonet connector 160 may include a proximal portion 162 shaped as a conical frustum that may be used for coupling with plastic tubing. The distal portion 164 of the connector may be generally cylindrical with a substantially flat surface that may serve as a sealing surface when the male bayonet is fully inserted into the female receiving connector 100. In other embodiments the distal portion 164 of the male connector may have other shapes. For example, in one embodiment, the distal portion 164 may have a frustum shape. Additionally, in some embodiments, a foremost edge 166 of the male connector 160 may have a chamfered edge. In some embodiments, the foremost edge 166 may have a curved shape.

The male connector also has an annular channel 168 located between the proximal and distal ends 162, 164. The annular channel 168 may have flat or beveled edges that may be used to engage the locking plate 120. For example, in some embodiments, edges may be beveled to form a 45-degree angle with respect to the axes of the lumens defined by the male connector. In other embodiments, the beveled edges may be perpendicular to the axes, rounded, or alternatively may define any angle between 0 and 90 degrees.

In some embodiments, a proximal surface 170 of the first area 150 may have a shape corresponding to the foremost edge 166 of the male bayonet connector 160. For example, the proximal surface 170 may be chamfered or curved. The shape of the foremost edge 166 of the male bayonet connector 160, the proximal surface 170 of the first area 150, and/or the profile lead-in 128 may aid in the movement of the locking plate 120 relative to the male bayonet connector 160.

Figure 7:
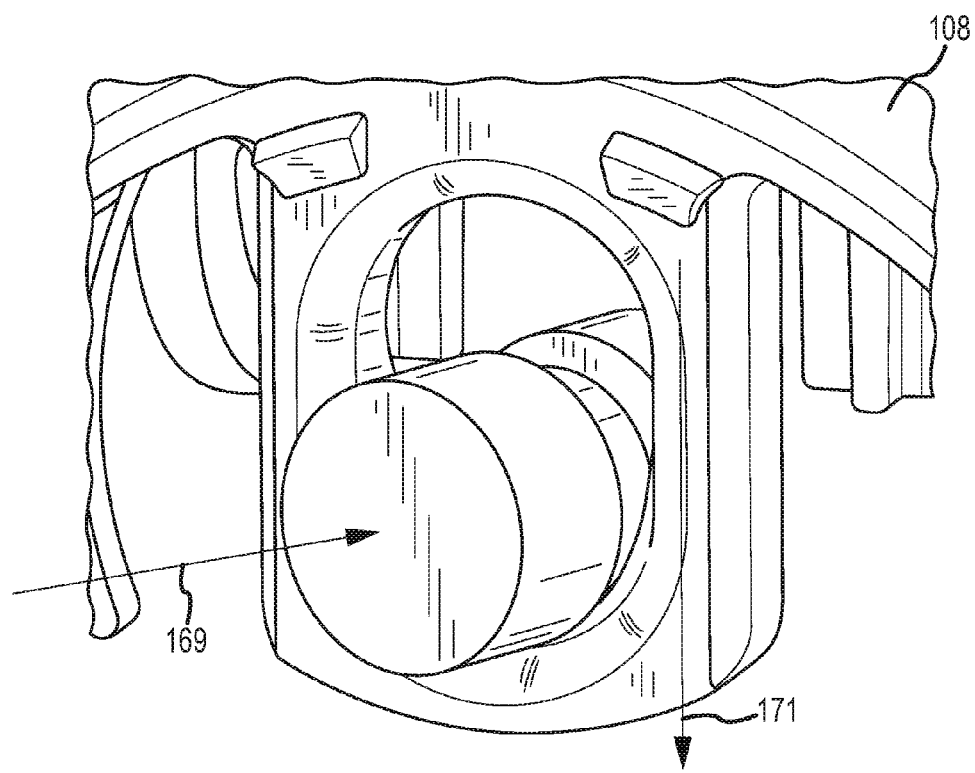
FIG. 7 illustrates the male bayonet connector of FIG. 6 interfacing with the locking plate to force the locking plate downward.
Figure 8:
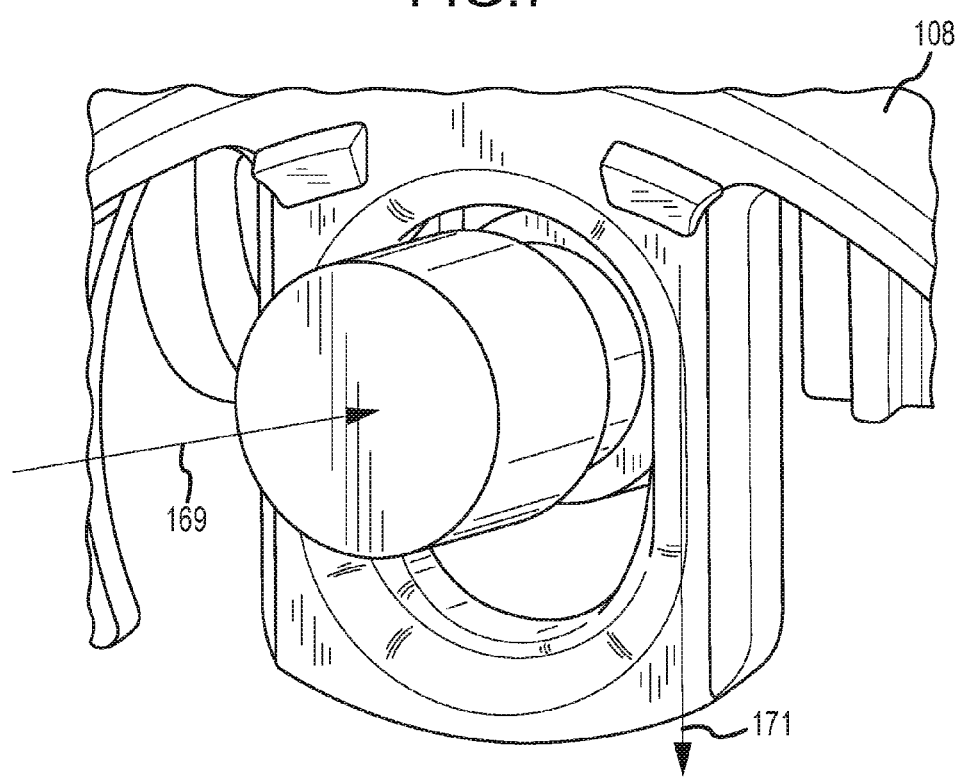
FIG. 8 illustrates the male bayonet connector of FIG. 6 pushing the locking plate fully downward and passing through the aperture of FIG. 5.
Figure 9:
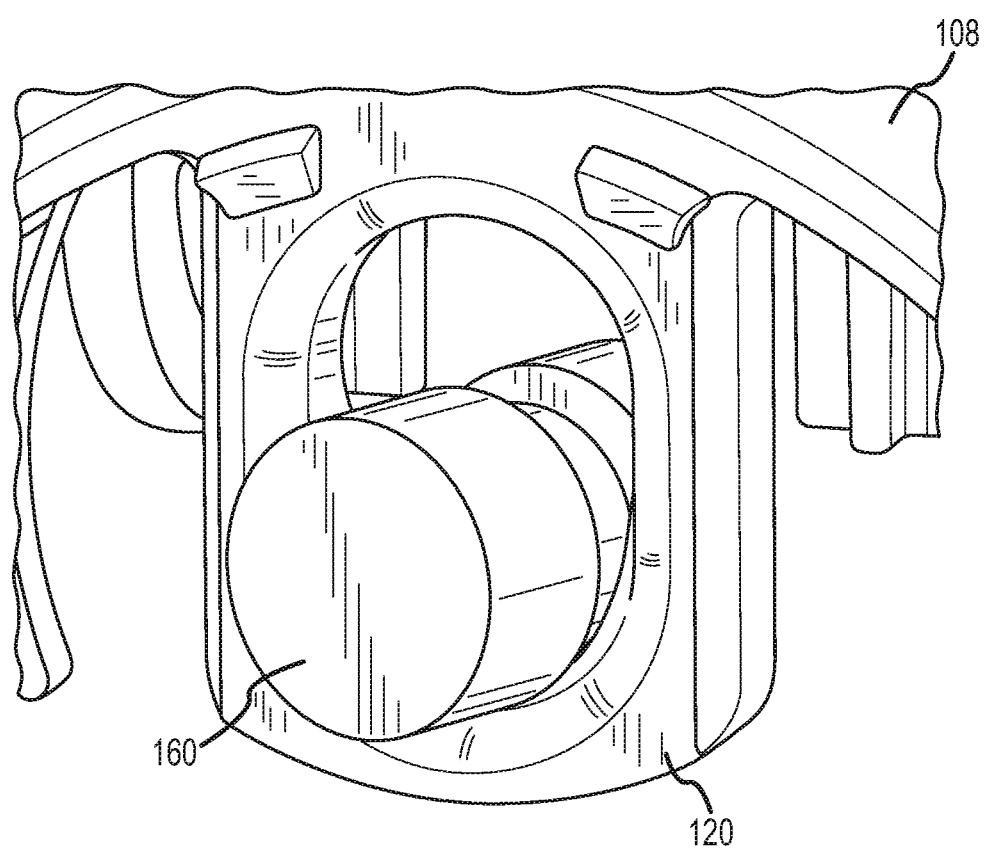
FIG. 9 illustrates the male bayonet connector of FIG. 6 secured by the locking plate.

As the male bayonet connector 160 enters into the housing 102, it contacts the proximal surfaces of the aperture 142. As pressure is applied to insert the male bayonet connector 160 through the aperture 142, as indicated by the arrow 169 (FIGS. 6, 7, and 8), the locking plate 120 is forced downward, as indicated by arrow 171 (FIGS. 7 and 8). In particular, because of the ramped profile lead-in 128, as pressure is applied to the locking plate 120 by pushing the male bayonet connector 160 into the aperture, the locking plate 120 is forced downward. The locking plate 120 continues downward until the male bayonet connector 160 is able to pass through the second aperture 158 (FIG. 8). The male bayonet connector 160 passes through the second aperture 158 until the channel of the male bayonet connector 160 is aligned with the profile lead-in 128. When the channel 168 is aligned with the profile lead-in 128, the locking plate 120 is pushed back upward by legs 130 and the profile lead-in 128 engages the channel 168 to secure the male bayonet connector 160 within the female receiving connector 100 (see FIG. 9).

The distal surface of the profile lead-in 128 may be shaped to hold the male bayonet connector 160 in place once installed. For example, in some embodiments, the distal surface of the profile lead-in may be flat. In other embodiments, the distal surface may be chamfered. The chamfered surface may facilitate the locking plate 120 engaging the channel 168 of the male bayonet connector. In some embodiments, the proximal surface and the distal surface may be chamfered. In another embodiment, one of the distal or proximal surfaces of the profile lead-in 128 is chamfered and the other surface is flat.

In some embodiments, the shape of the surfaces of the channel 168 may correspond with the surfaces of the profile lead-in 128. For example, in one embodiment, a distal surface of the channel 168 may be chamfered and the distal surface of the profile lead-in 128 may be chamfered. In some embodiments both the distal and proximal surfaces of the channel 168 may be chamfered. In some embodiments, both the proximal and distal surfaces of the channel 168 may be flat. In other embodiments, one of the proximal or distal surfaces may be chamfered and the other surface flat. In each instance, a shape of one or both surfaces of the channel of the male bayonet connector 160 correspond in shape with the corresponding the surface of the profile lead-in 128. That is, if the distal surface of the profile lead-in 128 is flat, the distal surface of the channel 168 is correspondingly flat. Additionally, the thickness of the profile lead-in 128 and the width of the channel of the male bayonet connector 160 are approximately the same.

When the male bayonet connector 160 is locked into place by the locking plate 120, a distal portion of the male bayonet connector 160 may be in contact with the sealing member 122 to form a seal between the sealing member 122 and the surface of distal portion 164 of the male bayonet connector 160.

The button 108 may be pressed downward to release the male bayonet connector 160 from the female receiving connector 100. Specifically, as the button 108 is pressed downward, the locking plate 120 moves downward until the male bayonet 160 may clear the profile lead-ins 128 and may pass through the second area 156.

As mentioned above, the female receiving connector 100 may be implemented in multi-lumen configurations. For example, the female receiving connector 100 may include two, three, or more lumens. For each lumen, a locking plate is provided. In some embodiments, one or more locking plates may be coupled together. Additionally, in some embodiments, one or more locking plates may be integrally formed with the button 108. In some embodiments, one or more locking plates may be independently formed and subsequently coupled to the button 108. Additionally, in some embodiments, a shape of one or more locking plates may include one or more different features from other locking plates. For example, in one embodiment, a first locking plate associated with a first lumen may have a chamfered proximal surface, while a second locking plate associated with a second lumen may have a curved proximal surface. In another example, the distal surface of the first locking plate may have a chamfered surface, while a distal surface of a second locking plate may have a flat surface.

Figure 10:
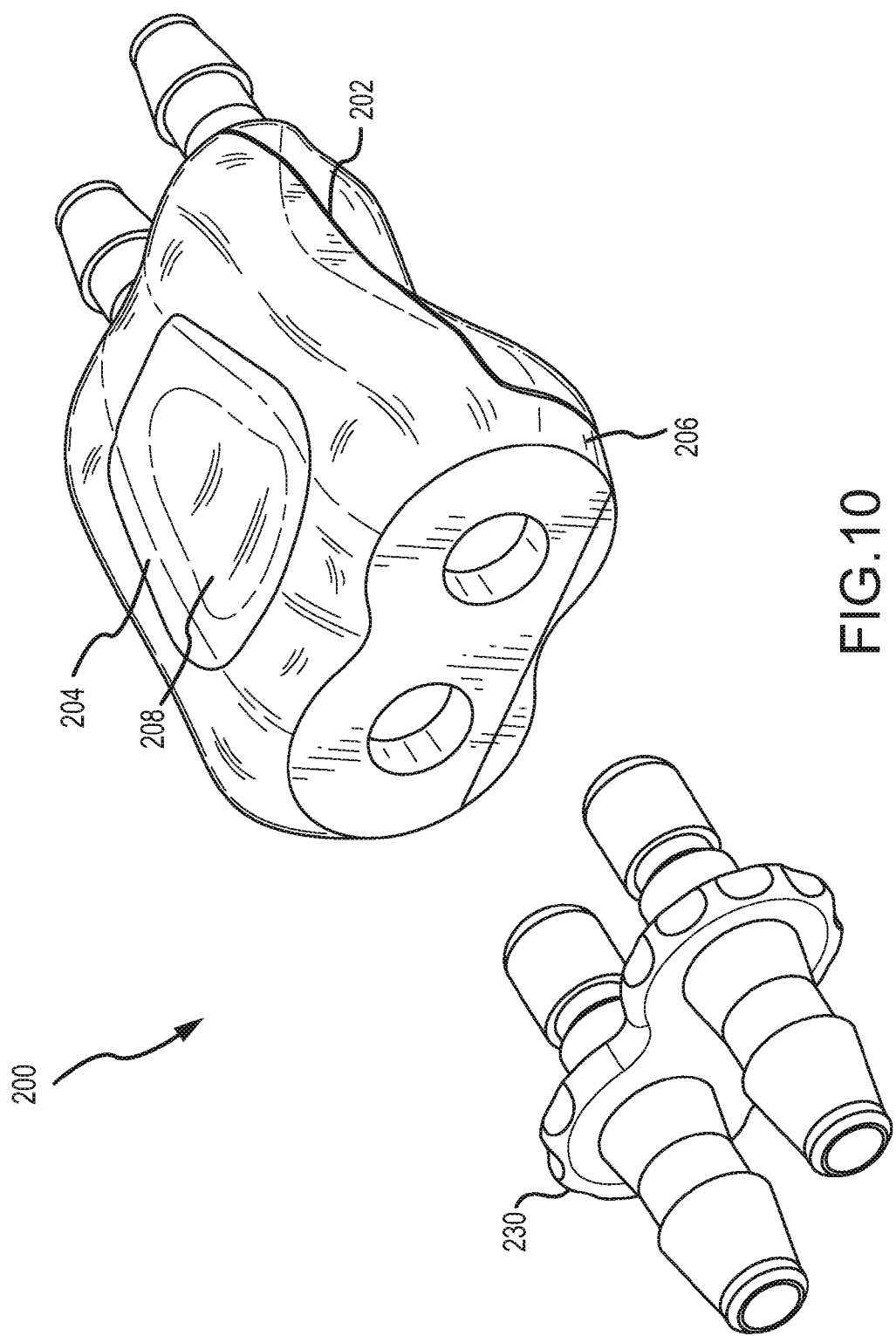
FIG. 10 illustrates a dual lumen female receiving connector in accordance with an alternative embodiment.

FIG. 10 illustrates a dual lumen female receiving connector 200 in accordance with an exemplary embodiment. In one embodiment, the dual female receiving connector 200 may be designed for connection between tubing from a blood pressure monitor and a male connector which is attached to tubing from a blood pressure cuff that may be fastened about a patient's arm. The dual lumen female receiving connector 200 allows for two air pathways within the connector. As with the single lumen discussed above, the dual lumen female receiving connector 200 includes a housing 202 that may include upper and lower portions 204, 206 and a button 208.

Figure 11:
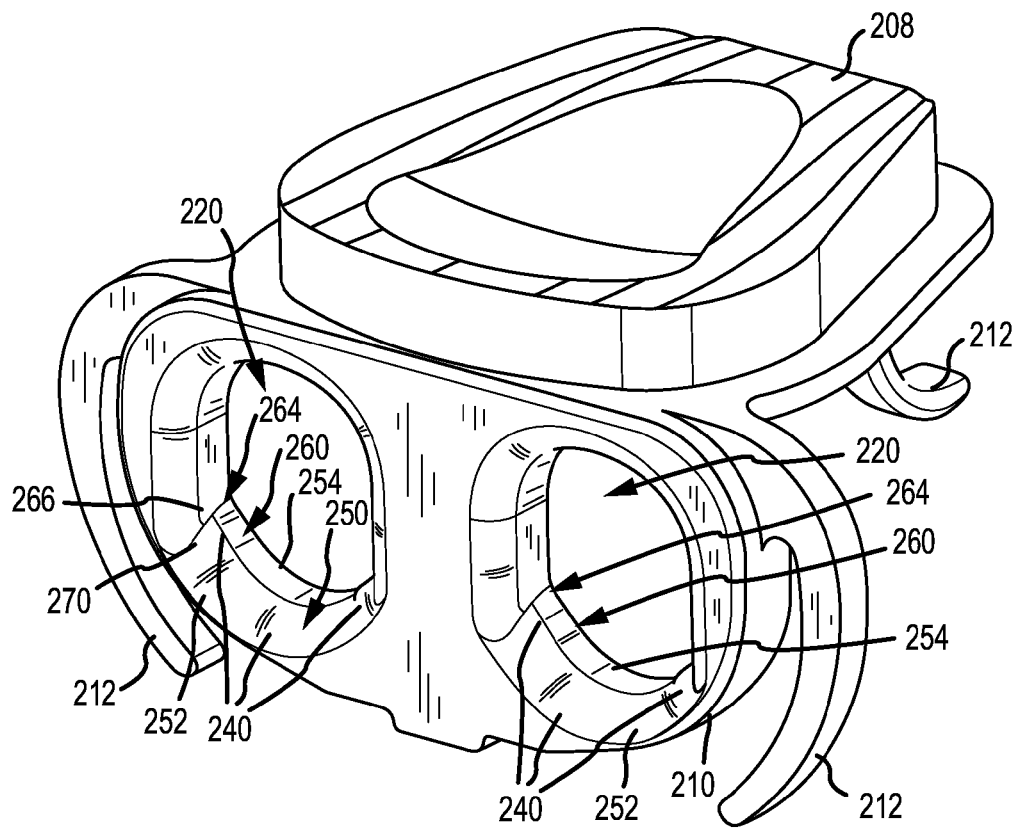
FIG. 11 is an isometric view of a button of the dual lumen female receiving connector of FIG. 10 with a locking plate having profile lead-ins.

FIG. 11 illustrates the button 208 with a locking plate 210 and legs 212. The legs 212 serve as spring members to hold the button 208 in a raised position within the housing 202. Additionally, the legs 212 provide a holding force to secure the male connector 230 in the female receiving connector when the two are coupled together. That is, the legs 212 hold the locking plate 210 in position while it engages the male connector 230.

The locking plate 210 includes two apertures 220, one for each lumen of the dual lumen female receiving connector 200. In some embodiments, the apertures 220 may be identical. That is, the apertures 220 may have the same or similar size and shape. In other embodiments, however, the apertures 220 may have different sizes and shapes. Additionally, in some embodiments, the lumens may be used to transport the same fluid, while in other embodiments, one lumen may transport a different fluid from the other.

Figure 12:
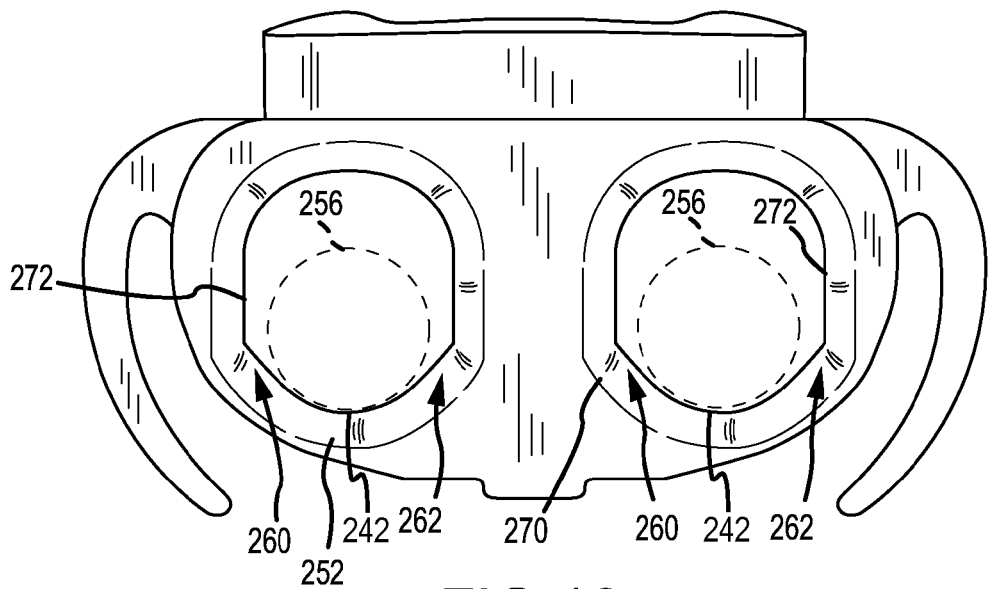
FIG. 12 is a front elevation view of the button of FIG. 11 illustrating an aperture of the locking plate.

The apertures 220 of the locking plate 210 are configured to facilitate the insertion of the male bayonet connectors 230 into the female receiving connector 200 while preventing their removal there from. As such, the apertures 220 are, in part, defined by curved profile lead-ins 240. The profile lead-ins 240 constitute a lower edge 242 of the apertures 220. The profile lead-ins 240 are shown in FIGS. 11 and 12 and generally may have regions which provide curved contours to facilitate insertion or securing of the male bayonet connector 230 within the female receiving connector 200. For example, in one embodiment, a center region 250 may include curved interfacing surface portion 252 that extends from a proximal edge of the locking plate 210 toward a substantially flat surface 254 formed as a parabolic cylinder surface on the interior of the apertures 220. A middle portion of the substantially flat surface 254 has a contour defined by a radius of a circle 256 (FIG. 12) that corresponds to the radius of the outer surface of the male bayonet connector 230. The radius of the contour may be larger or smaller as long as it can accept and interface with the channel of the male bayonet connector 230. The substantially flat surface 254 extends to left and right regions 260, 262. In the left and right regions 260, 262, the substantially flat surface 254 tapers toward a distal edge 264 of the locking plate 210. In one exemplary embodiment, the angle of the lead-in 240 is 45 deg., leading into a 0.020" radius to generally flat surface 254. As seen in FIG. 11, the substantially flat surface 254 may be formed with a slight (e.g., 0.097") radius. The substantially flat surface 254 transitions to a bulbous, radiused edge in left and right regions 260, 262 toward the edges of the aperture 220. The shape of the left and right regions 260, 262 is the primary factor to the ease of insertion of the male connector 230 as it rides over the bulbous surface, forcing the button to the "down" position.

The curved interfacing surface portion 252 also extends into the left and right regions 260, 262 as shown in FIG. 12. In the left region 260, for example, the curved portion 252 may have a convex contour. The convex contour may extend from the proximal edge 266 of the locking plate 210 towards its distal edge 264. Because of the tapering of the substantially flat surface 254 in the left region 260, the convex contour expands as it progresses from the center region 250 through the left region 260. An apex of the curved interfacing surface portion 252 is extended into the edge 272 of the aperture, forming a curved ledge 270. The right region 262 is generally a mirror image of the left region 260 and as such has similar features.

Referring to FIG. 12, the profile of the substantially flat surface 254 may be seen. As discussed above, the substantially flat surface 254 of the center region 250 may be defined by the circumference of a circle 256 that correlates with the circumference of the channel of the male bayonet connector 230. The substantially flat surface 254 of the left and right regions 260, 262, however, may have different profiles in different embodiments. For example, in one embodiment, the profile of the substantially flat surface 254 may be defined by a substantially straight line in the left and right regions 260, 262. In some embodiments, the profile may have a decreasing slope as it approaches the edge 272, defining a convex profile. In other embodiments, the profile may be slightly concave, but less so than the profile of the center region.

Figure 13:
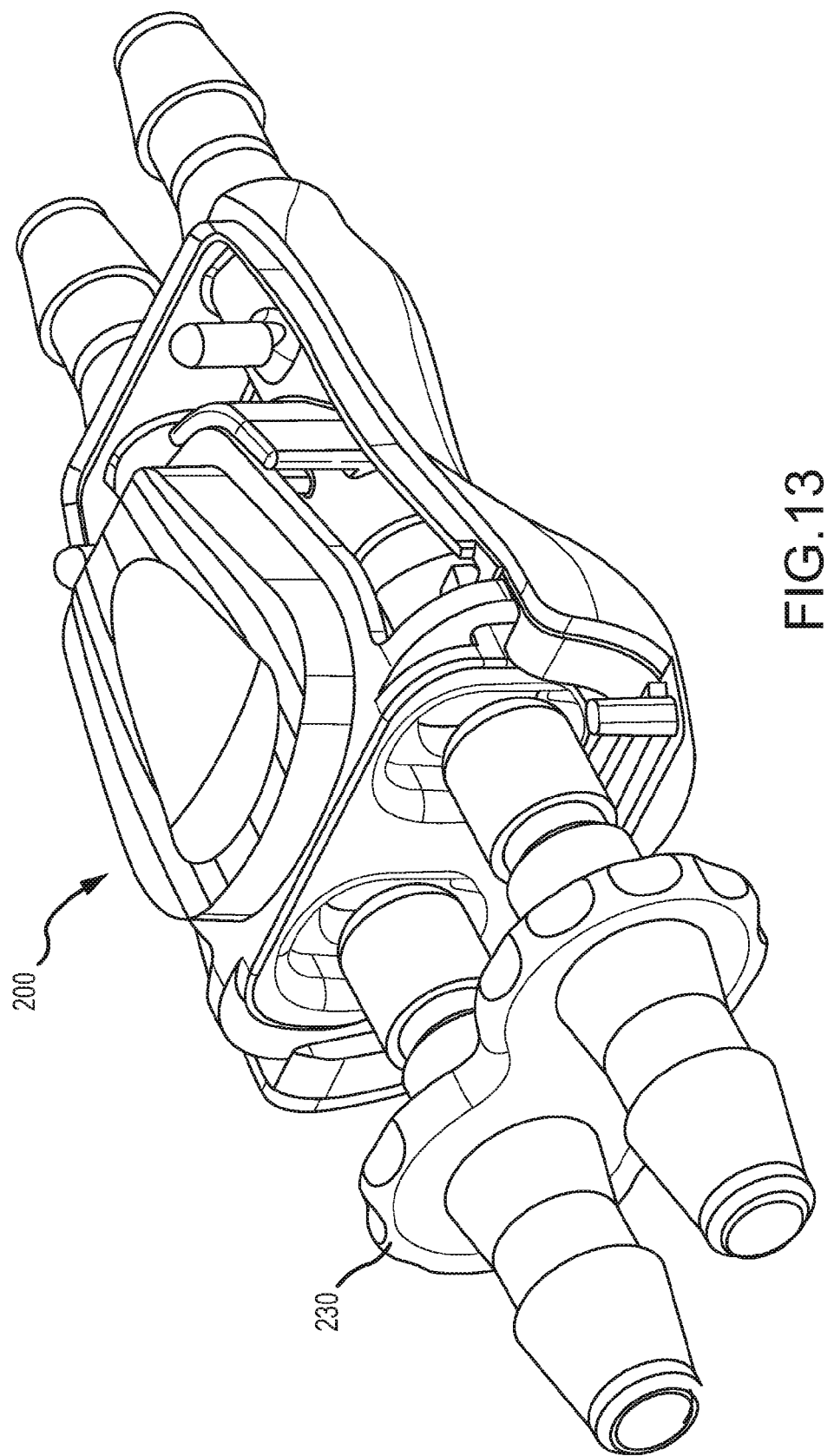
FIG. 13 illustrates a dual male bayonet connector entering the dual lumen female receiving connector of FIG. 10 with a top housing portion of the housing removed.
Figure 16:
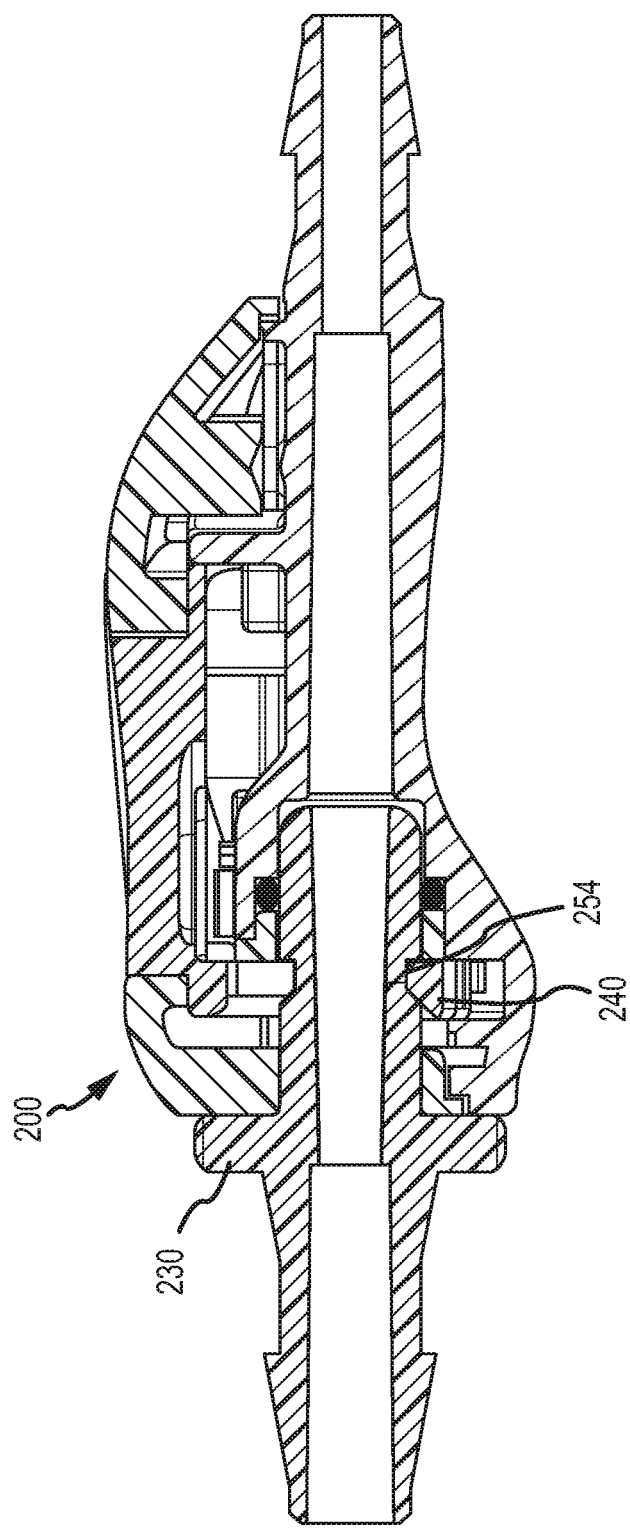
FIG. 16 is a cross-sectional view of the dual lumen male bayonet connector secured by a locking plate of the female receiving connector of FIG. 10.

The profile lead-ins 240 provide the initial contact surfaces for the male bayonet connector 230 during insertion. FIG. 13 illustrates the male bayonet connector entering the female receiving connectors 200. In FIG. 13, the top housing member is removed to show detail with in the housing. FIG. 14 is a cross sectional view showing the male bayonet connector 230 contacting the profile lead-in 240 of the center region 250. The contact of the profile lead-in 240 by the male bayonet connector 230 forces the locking plate 210 downward until the sealing surface of the male bayonet connector 230 is able to pass through the aperture 220, as shown in FIG. 15. The male bayonet connector 230 may further be inserted into the aperture 220 until the channel of the male bayonet connector 230 and the substantially flat surface 254 of the center region 250 engage (FIG. 16) to secure the male connector 230 within the female connector 200. When the male bayonet connector 230 is secured within the female receiving connector 200, a sealing member, such as a rubber O-ring, may contact a sealing surface of the male bayonet connector 230 to seal the lumen.

Figure 17:
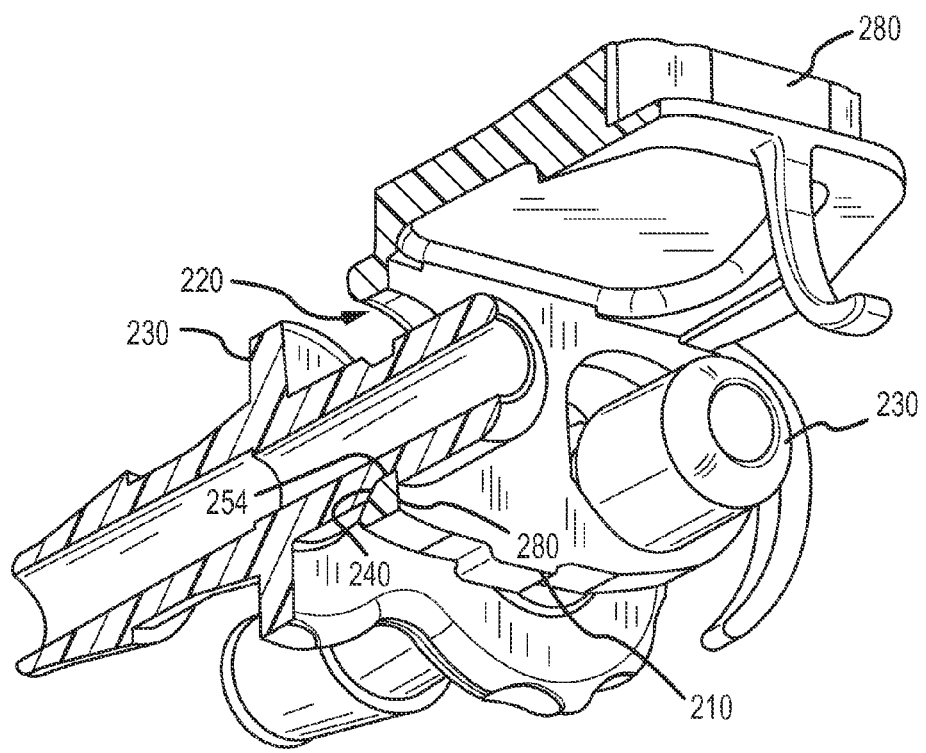
FIG. 17 illustrates a cross-sectional view from a distal perspective of the male bayonet connector secured by a locking plate of the female receiving connector of FIG. 10.

As illustrated in FIG. 17, the substantially flat surface 254 may perpendicularly adjoin a distal locking surface 280 of the profile lead-in 240 that is flat. That is, in one embodiment, the distal surface of the profile lead-in 240 defining the rear edge of the aperture 220 may be flat. In some embodiments, the distal locking surface 280 of the profile lead-in 240 and a distal surface of the locking plate 210 may be the same surface. In other embodiments, they may constitute different surfaces. A corresponding engagement surface of the channel may also be flat to help secure the male bayonet connector 230 within the female receiving connector 200. In other embodiments, the distal locking surface 280 of the locking plate 210 may take other forms. For example, in one embodiment, the distal surface 280 may be chamfered.

FIG. 17 is a partial cross sectional view from a distal perspective of the button 208 and the male bayonet connector 230 with the male bayonet connector secured within the locking plate 210. As can be seen, the male bayonet connector 230 is secured within the lower portion of the aperture 220 while the upper portion of the aperture is vacant. Additionally, the profile lead-in 240, the substantially flat surface 254, and the distal locking surface 280 of the locking plate 210 may each be in contact with the channel of the male bayonet connector 230 to secure the male bayonet connector.

Figure 18:
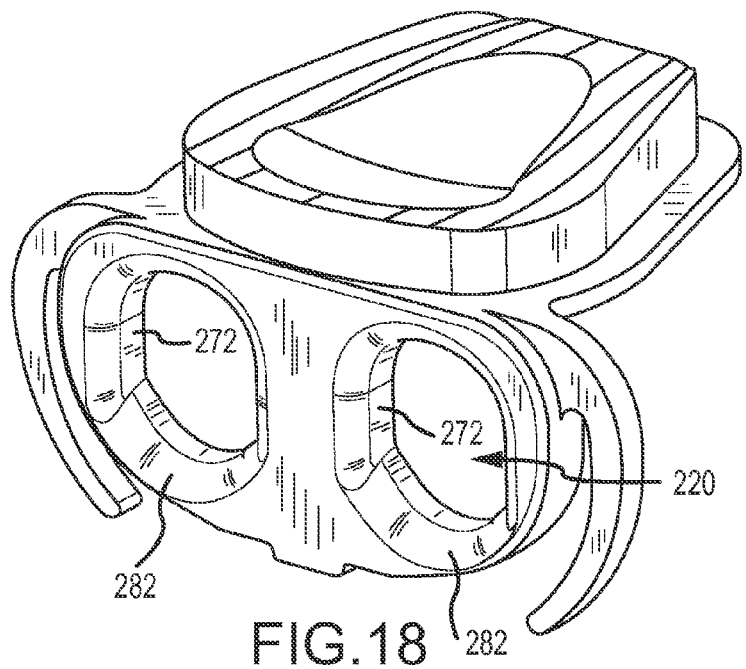
FIGS. 18-20 illustrate multiple embodiments of latch buttons having example alternative profile lead-ins for use in the female receiving connector of FIG. 10.
Figure 19:
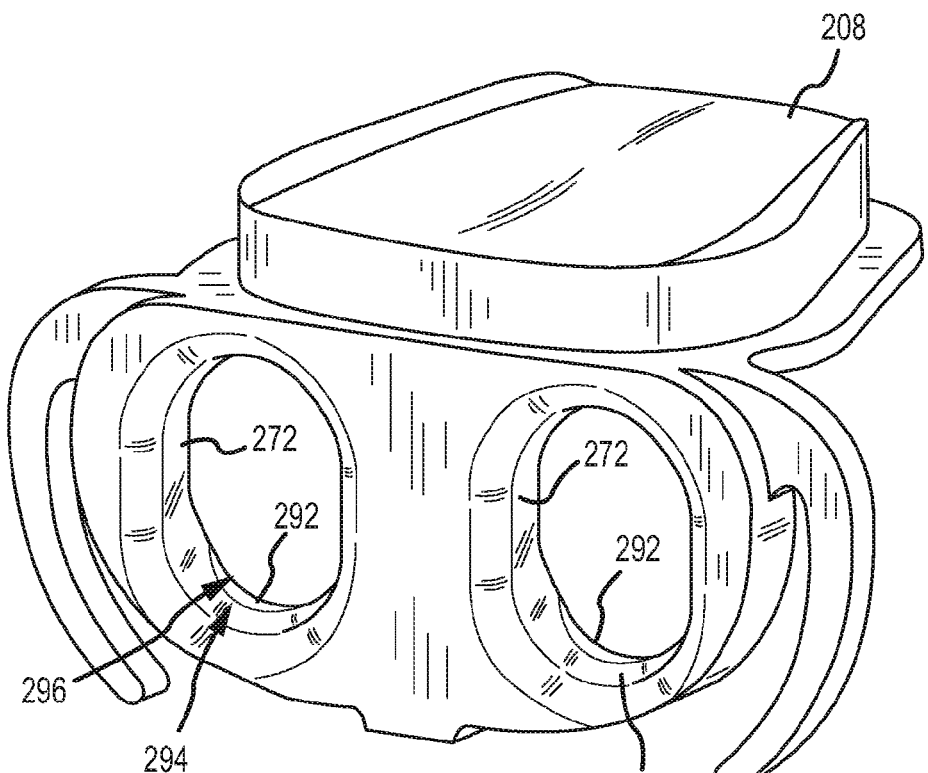
Figure 20:
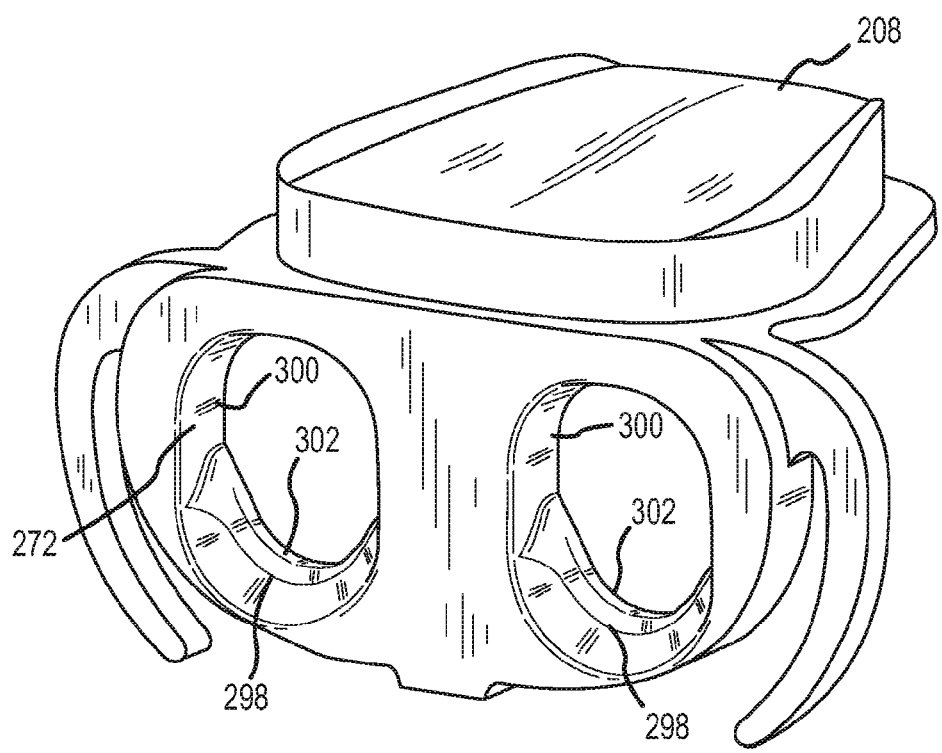

It should be appreciated that, in other embodiments, the profile lead-ins 240 may take other forms. FIGS. 18-20 illustrate alternative embodiments of the exemplary profile lead-ins. In particular, FIG. 18 illustrates embodiment having the same general characteristics as the embodiment shown in FIGS. 11 and 12, but with profile lead-ins 282 in left and right regions extending further up the edges 272 of the apertures 220. FIG. 18 has smaller "bulbous" radii in case the male shafts are molded on the large end of the tolerance range. The smaller radii will enable the male shafts to more easily glide on and force down the button latch. Thus, the profile lead-ins 282 in the left and right regions may have a more gradual contour when compared to the embodiments shown in FIGS. 11 and 12.

FIG. 19 illustrates an embodiment having a profile lead-in 290 with a continuous profile with very little side loft on a narrow and short flat engaging surface 292 in the form of a parabolic cylinder surface. That is, the entirety of the flat engaging surface 292 may have a profile defined by the circumference of a circle that corresponds to the circumference of the channel of the male bayonet connector 230. The substantially flat engaging surface 292 gradually tapers from the proximal edge 294 to the distal edge 296 of the locking plate 210 as it approaches the edges 272.

FIG. 20 illustrates an embodiment similar to the embodiments illustrated in FIGS. 11, 12, and 18, having profile lead-ins 298 with higher edge loft 300 than the form of FIGS. 18 and 19, but with lower loft than in the embodiment of FIG. 3. FIG. 20 has larger bulbous radii in case the male shafts are molded on the small side of the tolerance range. The larger bulbous radii will enable the interference between the lead-in 298 and the male shafts to occur at about the same male insertion depth compared to shafts molded to the nominal dimensions. The flat surface 302 in the form of a parabolic cylinder surface is wider than in the embodiment of FIG. 19 and extends into the edge 272 to form a ledge across the bottom of the aperture. In FIG. 20, the edges 272 are thick, flat, and straight.

The profile lead-in is designed to maintain a relatively low insertion force of the male connector while also maintaining a robust distal edge of the locking plate so that it locks/holds the male connector to the female receiving connector when fully inserted. Prototypes have been built of the various embodiments described above and experiments performed to confirm the male connector insertion force that actuates the locking plate downward to allow for insertion of the male connector is relatively low. Additionally, experiments were performed to confirm the axial pull force that results in the male connector decoupling from the female receiving connector when fully inserted and locked is relatively high.

It will be apparent to those of ordinary skill in the art that variations and alternative embodiments may be made given the foregoing description. Such variations and alternative embodiments are accordingly considered within the scope of the present invention. For example, a profile lead-in may be implemented with a curved portion to form a profile, profile lead in.

As used herein, lumen refers not only to its definition, but also refers to an opening, aperture, or other passageway. The fluid referred to herein can be gaseous, liquid, or other state of material that is flowable through a tube (i.e., granular). In addition, while generally described above as sealed when connected together, the connector structures may be sealed or unsealed. The connection between the male dual bayonet connector and female receiving connectors and their respective tube sections can be by means other than a barbed fitting, for example, but not limited to, threaded, press-fit without a barb, John Guest fitting, ferrule, and panel mount.

All directional references (e.g., upper, lower, upward, downward, left, right, leftward, rightward, top, bottom, above, below, inner, outer, vertical, horizontal, clockwise, and counterclockwise) are only used for identification purposes to aid the reader's understanding of the example of the invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A female receiving connector for connecting sections of tubing comprising
   a housing further comprising
      a top housing portion;
      a bottom housing portion coupled to the top housing portion; and
   a button moveably coupled within the housing; and
   a locking plate coupled to the button and configured to move with the button, the locking plate including at least a first surface profile and a second surface profile together defining an enclosed aperture, with the first surface profile having a profile lead-in further comprising
      an interfacing surface formed on a proximal side of the profile lead-in for interfacing with a male connector, wherein the interfacing surface extends along a bottom portion of the enclosed aperture of the locking plate;
      a locking surface located on a distal side of the bottom portion of the aperture for securing the male connector within the housing of the female receiving connector; and
      a parabolic cylinder surface located between the interfacing surface and the locking surface, wherein
      the parabolic cylinder surface extends to lateral edges of the aperture,
      a proximal edge of the parabolic cylinder surface tapers distally towards a distal edge of the parabolic cylinder surface as the parabolic cylinder surface approaches the lateral edges of the aperture such that a distance between the proximal edge and distal edge narrows, the interfacing surface has a length from a proximal edge of the interfacing surface to the proximal edge of the parabolic cylinder surface that varies from a center toward lateral edges of the aperture, a middle length at a center of the interfacing surface is shorter than an outer length of the interfacing surface at the lateral edges such that the interfacing surface becomes longer distally at the at the lateral edges while the parabolic cylinder surface becomes shorter proximally at the lateral edges, the distal edge of the parabolic cylinder surface abuts with the locking surface and the parabolic cylinder surface is perpendicular to the locking surface; and wherein
   the second surface profile defines a convex curved surface extending from a proximal side of the locking plate to a distal side of the locking plate.

2. The female receiving connector of claim 1, wherein the aperture of the locking plate comprises two overlapping areas; and
   a first area is defined by a circumference of a first circle that is smaller than a circumference of a second circle that defines a second area; whereby
   the female receiving connector is configured to allow the male connector to pass through the second area and secure the male connector within the first area.

3. The female receiving connector of claim 1, wherein the button and the locking plate are integrally formed.

4. The female receiving connector of claim 1, wherein the interfacing surface expands distally as the proximal edge of the parabolic cylinder surface extends distally.

5. The female receiving connector of claim 1, wherein the parabolic cylinder surface has a substantially constant profile from the proximal edge to the distal edge and a middle portion is defined by a radius of a circle that corresponds to a radius of an outer surface of the male connector.

6. A female receiving connector for transporting fluids comprising
   a housing defining at least one lumen for fluid flow, the housing further comprising
      a top housing portion; and
      a bottom housing portion coupled to the top housing portion; and
   a button moveably coupled within the housing and retained by the top housing portion, the button further comprising
      a locking member coupled to the button and configured to displace in conjunction with the button when force is applied to the button or to a surface of the locking member, the locking member including at least a first surface profile and a second surface profile together defining an aperture, wherein the first surface profile includes a profile lead-in defining an edge of the aperture, wherein the profile lead-in further comprises
      a curved surface formed on a proximal side of a bottom surface of the profile lead-in for interfacing with a male connector;
      a locking surface located at a distal side of the locking member adjacent the profile lead-in for securing the male connector within the housing of the female receiving connector; and
      a parabolic cylinder surface located between the curved surface and the locking surface, wherein
      a distal edge of the parabolic cylinder surface abuts with the locking surface and the parabolic cylinder surface is perpendicular to the locking surface;
      the curved surface extends from a proximal face of the locking member to the parabolic cylinder surface,
      the curved surface has a convex contour extending from the proximal face of the locking member to the parabolic cylinder surface,
      the curved surface extends below the aperture to lateral edges of the aperture, and the curved surface has a length from a proximal edge of the curved surface to the proximal edge of the parabolic cylinder surface that varies from a center toward the lateral edges of the aperture, a middle length at a center of the curved surface is shorter than an outer length of the curbed surface at the lateral edges such that the curved surface becomes longer distally at the at the lateral edges while the parabolic cylinder surface becomes shorter proximally at the lateral edges such that a distal edge of the curved surface diverges away from a proximal edge of the curved surface as the curved surface approaches the lateral edges of the aperture, and wherein
   the second surface profile includes a curved surface extending from the proximal side to the distal side.

7. The female receiving connector of claim 6, wherein
the parabolic cylinder surface extends to lateral edges of the aperture; and
a proximal edge of the parabolic cylinder surface tapers distally at the lateral edges such that a distance between the proximal edge and distal edge narrows.

8. The female receiving connector of claim 6, wherein an apex of the curved surface extends into the lateral edges of the aperture forming a curved ledge.

9. The female receiving connector of claim 6, wherein the curved surface terminates at the lateral edges of the aperture.

10. The female receiving connector of claim 6, wherein the parabolic cylinder surface has a substantially constant profile from a proximal edge to a distal edge thereof and a middle portion is defined by a radius of a circle that corresponds to a radius of an outer surface of the male connector.

11. The female receiving connector of claim 6, wherein the locking surface of the profile lead-in is the same as a distal surface of the locking member.

* * * * *

UNITED STATES PATENT AND TRADEMARK OFFICE
CERTIFICATE OF CORRECTION

PATENT NO. : 9,046,205 B2  
APPLICATION NO. : 12/976894  
DATED : June 2, 2015  
INVENTOR(S) : Whitaker et al.

It is certified that error appears in the above-identified patent and that said Letters Patent is hereby corrected as shown below:

In the claims

Claim 1, column 11, line 46, delete the second occurrence of "at the"

Claim 6, column 12, line 57, "curbed" should read "curved"

Claim 6, column 12, line 59, delete the second occurrence of "at the"

Signed and Sealed this  
Sixteenth Day of February, 2016

Michelle K. Lee  
*Director of the United States Patent and Trademark Office*